United States Patent
Huang et al.

(10) Patent No.: US 10,692,591 B2
(45) Date of Patent: Jun. 23, 2020

(54) APPARATUS, METHOD AND COMPUTER READABLE MEDIUM FOR TRACKING DATA AND EVENTS

(71) Applicant: B-LINE MEDICAL, LLC, Washington, DC (US)

(72) Inventors: Lucas K Huang, Ellicott City, MD (US); Chafic A Kazoun, Washington, DC (US); Anton D Kropp, Seattle, WA (US); Samuel R Neff, Rockville, MD (US); David A Ramsay, Durham, NH (US)

(73) Assignee: B-Line Medical, LLC, Washington, DC (US)

( * ) Notice: Subject to any disclaimer, the term of this patent is extended or adjusted under 35 U.S.C. 154(b) by 179 days.

(21) Appl. No.: 14/171,185

(22) Filed: Feb. 3, 2014

(65) Prior Publication Data
US 2014/0222805 A1 Aug. 7, 2014

Related U.S. Application Data

(60) Provisional application No. 61/759,752, filed on Feb. 1, 2013, provisional application No. 61/798,359, filed on Mar. 15, 2013.

(51) Int. Cl.
*G06F 16/903* (2019.01)
*G16H 10/60* (2018.01)

(52) U.S. Cl.
CPC ....... *G16H 10/60* (2018.01); *G06F 16/90335* (2019.01)

(58) Field of Classification Search
None
See application file for complete search history.

(56) References Cited

U.S. PATENT DOCUMENTS

| 5,842,978 | A | 12/1998 | Levy | |
|---|---|---|---|---|
| 7,610,083 | B2 | 10/2009 | Drew et al. | |
| 8,676,027 | B2 | 3/2014 | Hugosson | |
| 2002/0138512 | A1* | 9/2002 | Buresh | G06F 19/3406 715/214 |
| 2006/0106767 | A1* | 5/2006 | Adcock | G06F 17/30613 |
| 2007/0271122 | A1* | 11/2007 | Zaleski | A61B 5/1113 705/3 |
| 2008/0123915 | A1* | 5/2008 | Nagy | G06F 19/321 382/128 |
| 2008/0145830 | A1* | 6/2008 | Huang | G09B 9/00 434/336 |

(Continued)

*Primary Examiner* — Giuseppi Giuliani
(74) *Attorney, Agent, or Firm* — Sughrue Mion, PLLC

(57) ABSTRACT

A methods, an apparatus, a computer-readable medium, and a system for integrating data from a plurality of devices. The first data is received from a first device and the second data is received from a second device, which is a different type of device than the first device. Type of data is determined and additional data is generated based on the determined type of data received from these different devices. The additional data includes searchable metadata and/or one or more triggers based on a combination of the first and second received data. Accordingly, searchable metadata for recordings and metric values from various devices used in a session are generated. Additionally, annotations may be provided to emphasize the occurrence of triggering events.

22 Claims, 16 Drawing Sheets

(56) References Cited

U.S. PATENT DOCUMENTS

| | | | | |
|---|---|---|---|---|
| 2009/0005650 A1* | 1/2009 | Angell | ................... | G06Q 10/10 705/3 |
| 2011/0305376 A1* | 12/2011 | Neff | ...................... | G16H 40/20 382/128 |
| 2013/0182107 A1* | 7/2013 | Anderson | .............. | G08B 21/02 348/143 |

* cited by examiner

| TYPE | METADATA |
|---|---|
| VIDEO | DATE AND TIME, PATIENT ID, TITLE, TYPE, SOURCE OF RECORDING |
| AUDIO | DATE AND TIME, PATIENT ID, TITLE |
| METRIC VALUES | DATE AND TIME, PATIENT ID, SOURCE OF DATA, TYPE |
| IMAGES | DATE AND TIME, PATIENT ID, SOURCE OF DATA, BODY PART, ILLNESS |

FIG. 5B

User, Demo ▼ livecapture

Search [____]  [Hide Advanced]

| | | |
|---|---|---|
| Data Stat ▶ | SBP | between 140 and 210 ○ |
| Data Stat ▶ | DBP | between 90 and 125 ○ |
| Data Stat ▶ | CBF | less than 50 ○ |
| Data Stat ▶ | Age | between 40 and 60 ○ |
| Select One... ▶ | | [____] ○ |

509

[Clear]  [Apply]

510

| | Session Start | Duration | Location |
|---|---|---|---|
| aussig: User | January 07, 2011 11:32 AM | 3m 31s | HE - ICU |
| aussig: User | January 07, 2011 10:57 AM | 4m 7s | HE - ICU |
| aussig: User | January 07, 2011 10:47 AM | 3m 51s | HE - ICU |
| aussig: User | January 07, 2011 12:15 AM | 3m 53s | HE - ICU |
| | January 07, 2011 12:09 AM | 1m 53s | HE - ICU |
| | January 05, 2011 2:22 PM | 2m 47s | HE - Skills Lab |
| | January 05, 2011 2:20 PM | 1m 18s | HE - Skills Lab |
| | January 05, 2011 2:17 PM | 1m 47s | HE - Skills Lab |
| | January 05, 2011 2:11 PM | 1m 9s | HE - Skills Lab |
| | April 16, 2010 8:39 AM | 1m 6s | SoM - Skills Lab |
| | April 16, 2010 8:32 AM | 59s | SoM - Skills Lab |
| | April 16, 2010 8:19 AM | 2m 13s | HW - OR |
| | April 04, 2010 6:32 AM | 4m 23s | HW - ICU |
| | April 04, 2010 6:28 AM | 2m 40s | HW - OR |
| | April 04, 2010 6:20 AM | 2m 18s | HW - OR |
| | April 04, 2010 5:52 AM | 51s | HW - OR |
| | February 07, 2009 4:27 AM | 1m 57s | HW - Skills Lab |
| | February 07, 2009 4:17 AM | 2m 13s | HW - Skills Lab |
| | February 07, 2009 3:41 AM | 3m 12s | HW - Skills Lab |
| | February 07, 2009 3:19 AM | 3m 15s | HW - Skills Lab |
| | February 07, 2009 3:07 AM | 1m 34s | HW - Skills Lab |

```
┌─────────────────────────────────┐
│      GENERATE TRIGGER           │
│                                 │
│   NAME                          │
│   ┌─────────────────┐           │
│   │ TRIGGER 1_      │           │
│   └─────────────────┘           │
│                                 │
│   OUTPUT 1                      │
│   ┌─────────────────┐           │
│   │ HEART RATE      │           │
│   └─────────────────┘           │
│   ☒ Auto Record   ┌─────────┐   │
│                   │ <60,>115│   │
│                   └─────────┘   │
│   ☒ Past Record   ┌─────────┐   │
│                   │ 20 min  │   │
│                   └─────────┘   │
│                                 │
│   OUTPUT 2                      │
│   ┌─────────────────┐           │
│   │ OXYGEN LEVEL    │           │
│   └─────────────────┘           │
│   ☒ Auto Record   ┌─────────┐   │
│                   │  <80    │   │
│                   └─────────┘   │
│   ☒ Past Record   ┌─────────┐   │
│                   │ 20 min  │   │
│                   └─────────┘   │
│                        ┌───┐— SELECT DEVICE
│   ⋮                    │   │    TO TRIGGER
│   OUTPUT N    ┌───┐    └───┘   │
│               │ADD│    ┌────┐  │
│               └───┘    │ OK │  │
│                        └────┘  │
└─────────────────────────────────┘
```

FIG. 12

APPARATUS, METHOD AND COMPUTER READABLE MEDIUM FOR TRACKING DATA AND EVENTS

CROSS-REFERENCE TO RELATED APPLICATION

This application claims benefit pursuant to 35 U.S.C. §120 of the filing date of the Provisional Application Ser. No. 61/759,752 filed on Feb. 1, 2013 and titled "DATA, EVENT TRACKING, AND AUTOMATED RECORDING" and the Provisional Application Ser. No. 61/798,359 filed on Mar. 15, 2013 and titled "DATA, EVENT TRACKING, AND AUTOMATED RECORDING", which are incorporated herein by reference for all that they disclose in their entirety.

BACKGROUND

1. Field

Apparatuses, methods, and computer readable mediums consistent with exemplary embodiments relate to tracking data and events, and more specifically, to tracking data and events in one or more sessions for data analysis.

2. Description of the Related Art

To combine data from different sources (monitoring equipment) for centralized analysis such as quantifiable analysis and management, various analytical applications are developed.

For example, U.S. patent application Ser. No. 11/611,792 filed Dec. 15, 2006 by Lucas Huang and Chafic Kazoun titled Synchronous Multi-Media Recording and Playback with End User Control of Time, Data, and Event Visualization for Playback Control Over a Network describes such an analytical application. The disclosure of this application, application Ser. No. 11/611, 792 is incorporated herein by reference in its entirety.

For example, U.S. patent application Ser. No. 12/950,580 filed Nov. 19, 2010 by Chafic Kazoun, et. al. titled Apparatus, Method, and Computer Readable Medium for Simulation Integration describes a way to integrate data from multiple devices. The disclosure of this application, application Ser. No. 11/611, 792 is incorporated herein by reference in its entirety.

Accordingly, multiple different data sources and various analytical applications exist for managing the data from these data sources.

Currently within the healthcare IT environment and other environments, a related art system can capture data events during a session from various sources, including different medical devices from different manufacturers and/or information displays/records. One method of data capture is via optical character recognition (OCR). Command-based data capture to text is another method, whereby a command can be spoken, gestured (i.e. wave of hand), or triggered (i.e. via push of a button). Once a command is given, the system would wait for a speech input that would be converted to text and stored in the system. Each data event is associated with a specific time during a session. Currently, these data events are displayed on a graph with each variable represented as its own trend line, e.g. heart rate and blood pressure. While debriefing a session, the events are "played back" with the video. Often, the data captured and displayed may not necessarily be an event, but rather informative data, such as that displayed on an electronic medical record (patient's name, weight, age, presenting ailment, doctor, etc.). While not "playable" with video, this data is associated with the session and is useful to help search and track sessions.

In the related art, the systems do not provide a way to allow a user to combine these various elements or events and to search and track data over multiple sessions. In the related art, there is a need to process the data to improve tracking, monitoring, and/or searching of the data.

SUMMARY

According to exemplary, non-limiting embodiments, the system allows for searching one or more sessions based on a combination of data/data events from one or more of the different devices. Furthermore, the exemplary system allows the tracking of the frequency of these data events over a user-defined length of time.

Further, according to exemplary, non-limiting embodiments, the system also allows users to add annotations during a session in order to mark points of interest, which can then be used for tracking or as search criteria. Moreover, in an exemplary system, for a given search, an annotation may automatically be added to the point(s) in time that match the search criteria during playback.

According to an aspect of exemplary embodiments, a method of integrating data from a plurality of devices is provided. The method includes receiving first data from a first device, receiving second data from a second device different type of device with respect to the first device, determining, by a computer, type of the first received data and the second received data, and generating additional data based on the determined type of the first and second received data. The additional data includes at least one of searchable metadata and a trigger based on a combination of the first and second received data.

According to yet another aspect of exemplary embodiments, an apparatus configured to integrate data generated by a number of different devices is provided. The apparatus includes a processor configured to execute instructions and a memory configured to store these instructions. The instructions include receiving first data from a first device, receiving second data from a second device different type of device with respect to the first device, determining type of the first received data and the second received data, and generating additional data based on the determined type of the first received data and the second received data. The additional data includes at least one of searchable metadata and a trigger based on a combination of the first received data and the second received data.

According to yet another aspect of exemplary embodiments, a non-transitory computer readable medium storing instructions when executed by a computer cause a computer to perform various operations is provided. The operations include receiving first data from a first device, receiving second data from a second device different type of device with respect to the first device, determining by a computer type of the first received data and the second received data, generating additional data based on the determined type of the first received data and the second received data. The additional data includes at least one of searchable metadata and a trigger based on a combination of the first and second received data.

According to yet another aspect of an exemplary embodiment, a system for processing data from a plurality of devices is provided. The system includes at least one monitoring equipment configured to monitor output from at least one of an object and a human during a session, at least one audio or video recorder configured to record the at least one of the object and the human during the session, and a server including at least one processor and a memory. The server is configured to receive data from the at least one monitoring equipment and the at least one audio or video recorder, to determine type of an apparatus based on the received data, and to generate additional data based on the determined type of the apparatus.

BRIEF DESCRIPTION OF THE DRAWINGS

The accompanying drawings, which are incorporated in and constitute a part of this specification exemplify the exemplary embodiments and, together with the description, serve to explain and illustrate exemplary embodiments. Specifically:

FIG. 12 is a view illustrating a user interface for generating a trigger according to an exemplary embodiment.

DETAILED DESCRIPTION OF EXEMPLARY EMBODIMENTS

Products, manufactured by B-Line Medical®, enhance medical procedures, whether simulated or live, by recording sessions and integrating data from medical devices with video recordings and capture of a patient monitor or other display source but they are not limited thereto. The data management portion is managed by an integration engine ("Integration Engine") that connects with a range of medical devices from numerous manufacturers. Software Development Kit ("SDK") components allow manufacturers to develop robust and reliable integration with products of B-Line Medical® by working with a stable, well documented application programming interface ("API"). In an exemplary embodiment, the sessions may occur in a live setting such as a surgery in a hospital or a manufacture of a product at a production line. In yet another exemplary embodiment, the sessions may occur in a simulated environment.

Figure 1:
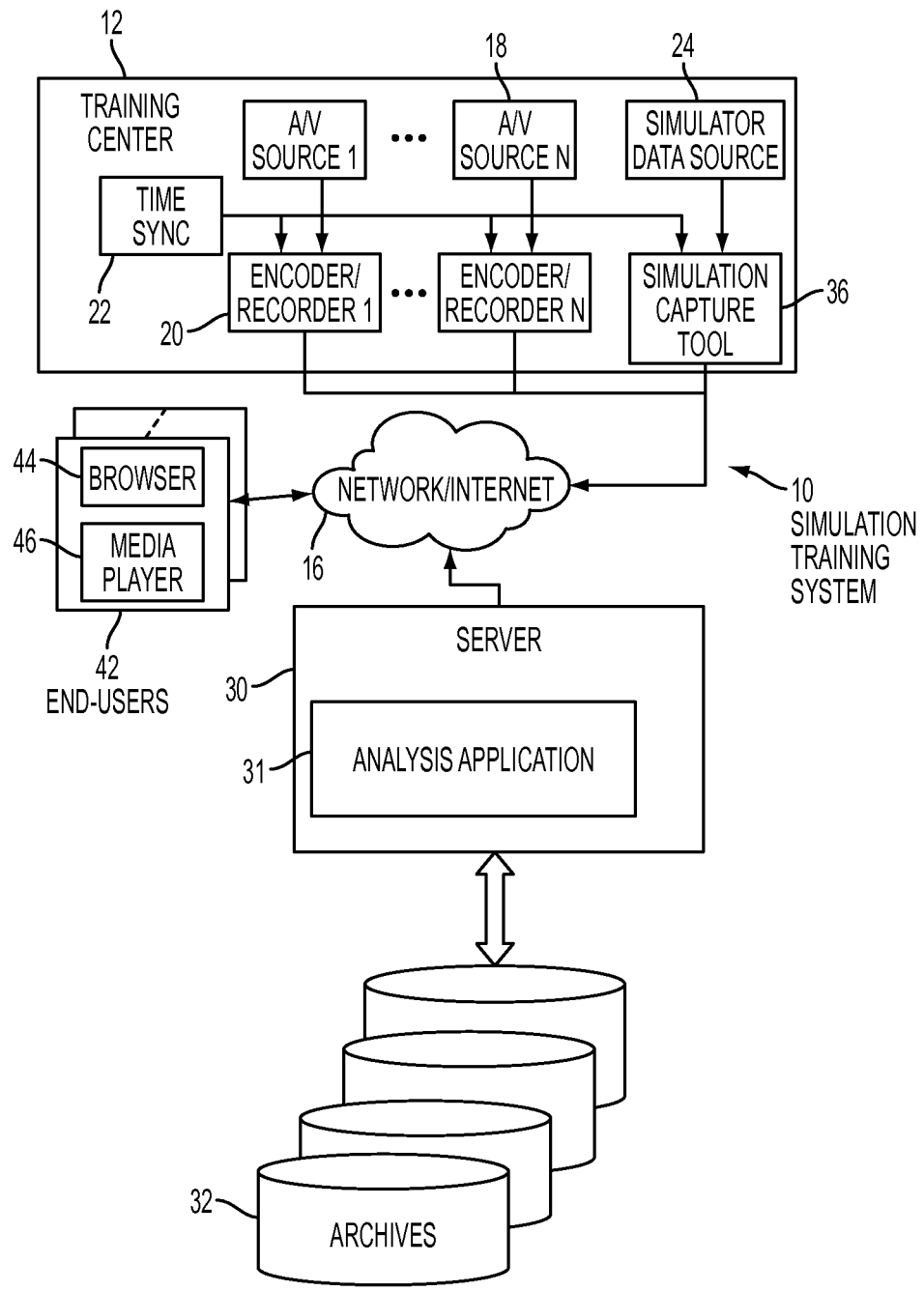
FIG. 1 is a block diagram illustrating a simulation training system in accordance with an exemplary embodiment.

FIG. 1 is a block diagram illustrating a simulation training system in accordance with an exemplary embodiment. An exemplary embodiment provides a web-based simulation training system 10 for providing synchronous multimedia recording and playback of recorded training sessions. The simulation training system 10 includes a training center 12 that has equipment for communicating with an analysis application 31 over a network 16, such as Internet. The training center 12 conducts and records simulation training sessions in one or more training rooms equipped with multiple audio/video (A/V) sources 18, multiple encoder/recorders 20, a time sync generator 22, and a simulator data source 24.

The training sessions are recorded using the A/V sources 18 and the data is sent to respective encoders/recorders 20. The A/V sources 18 in an exemplary embodiment are video cameras, but A/V sources 18 include any type of capture device, such as an auxiliary microphone or a still camera, and the like. The training sessions involve one or more trainees (not shown) who perform simulated procedures, or otherwise interact with, at least one simulator data source 24 that outputs real-time data in response. In an exemplary embodiment, real-time data may include actions/events occurring at the current time as well as those that occur within the context of a session. That is to say that the data is not post-processed or collected first, then manipulated after the session is complete. The real-time data may be processed on the fly.

The type of training conducted by the training center 12 will be described in terms of medical training that would be suitable for doctors, nurses, and emergency response personnel, but the exemplary embodiments are applicable in any type of training that involves the use of any type of simulator and any type of procedures that involve processing of data from various input devices.

Exemplary types of data sources 24 in the medical industry include full-body mannequin simulators, virtual reality simulators, EKG machines, and blood pressure monitors, patient monitors, and so on. However, the data source 24 may be a device or a machine used in an actual procedure performed in a hospital and not related to training. Also, the data source 24 may be a device unrelated to the medical field e.g., sales training device in a corporate environment or a monitoring device in a security system.

The encoders/recorders 20 and the simulation capture tool 36 may be remotely located from the training center, e.g., at the physical location of the server 30 or at another location.

A server (or a number of servers) 30, which is one or more computers that has a processor such as a CPU and a memory, is provided for running the analysis application 31. The analysis application 31 is software that analyzes real time data. That is, the analysis application 31 may process, categorize, and store categorized, sorted data into one or more databases. The analysis application 31 may also generate new data such as alarms and so on. The analysis application 31 may also include a skills assessment tool. The skills assessment tool provides a debrief tool and an annotation and assessment tool. The analysis application 31 may be implemented as a custom application that is installed at the training center 12, and accessed directly by clients i.e., end users 42 over a network such as the Internet 16.

The analysis application 31 accesses various data stored in databases/archives 32 such as a session data archive, a simulation data archive, and a multimedia archive and so on. This is provided by way of an example only and not by way of a limitation. In yet another exemplary embodiment, the data from various devices e.g., medical devices, may be received via Internet e.g., in a secure manner by an apparatus that has a memory and a processor. The processor of the apparatus may execute the analysis application and store data from the various medical devices in a local memory.

For example, in response to a training session being conducted, the system synchronously records in real-time both simulator data from a simulator data source 24 captured by a simulator capture tool, and video of the training session captured by a plurality of the A/V sources 18. The simulator data may be metric data obtained directly from a simulator or medical equipment e.g., blood pressure of the patient at time t1, heart rate in a period of time t2, etc. The simulator data is captured by the simulation capture tool 36. The time sync generator 22 is coupled to the encoders/recorders 20 and to the simulator capture tool 36, to control the synchronization of the recordings.

During the recording, each of the videos captured by A/V sources 18 are encoded as respective digital media files in streaming media format. Streaming media is media that is consumed (heard and/or viewed) while the media is being delivered. The videos captured by the A/V sources 18 may be encoded by the encoders/decoders 20. The simulator data may be captured in its raw and/or compressed format. In another exemplary embodiment, the simulator data can be captured using one of the A/V sources 18 by recording a video of the output of the simulator itself, e.g., by capturing a video of an EKG display. The simulation data may be encoded by the simulation capture tool 36.

During recording of the training session, the simulation data and the digital media files of the video and/or audio feeds are transmitted to the analysis application 31. The simulation data is sent to the analysis application by the simulation capture tool 36, where it is stored in the simulation data archive 32 and indexed by an ID of the training session. The video media files are sent to the analysis application 31 by the encoders/recorders and are stored in the multimedia archives 32.

Both the simulator data and a stream of the video media files may be transmitted to the end users 42 over the network 16, such that when the end users 42 receives the simulator data and the stream, the respective videos are synchronously played back with the simulator data on a device of the end user 42 using a browser 44 and a media player 46.

Each of the A/V sources 18 may be providing different data in different formats. Also various simulator data sources 24 may have different formats for various data, which is processed and normalized and provided to a server 30 for storage in the archives/databases 32. For example, the simulator data may include physiological statistics that are sent to the database 32 every time a change occurs e.g., blood pressure, oxygen level, heart rate, and so on. The rate at which data is sent to the database 32 is configurable, e.g. once per second, once per millisecond, and so on. The change may be transmitted in the form of raw data including numeric values for example "140, 90" for blood pressure. The data may then be stored in archives/databases 32.

In another exemplary embodiment, the encoder/recorder 20, analysis application 31, and datastores/archives 32 exist in a single self-contained and functioning device e.g., a tangible processing apparatus with a processor and a memory. This allows a session to run without needing communication to other servers or data archives.

In another exemplary embodiment, the self-contained device described above can exist as one of multiple devices that communicate with a central server. While each device functions on its own, if connected to the network, it will simultaneously send data to the central server. The central server, then, will contain data from all of its networked devices. The central server also contains an analysis application.

Figure 2:
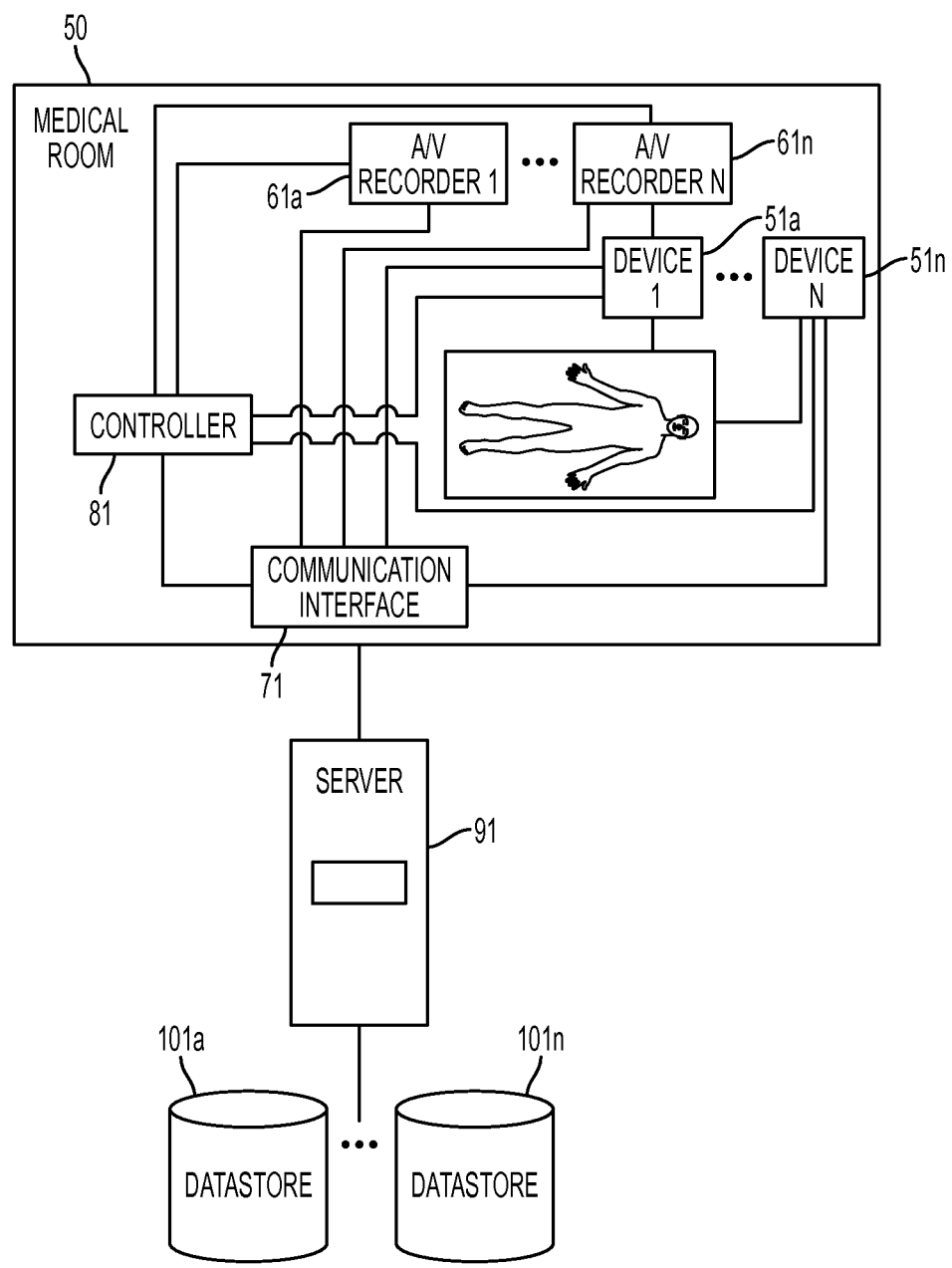
FIG. 2 is a block diagram illustrating a medical system according to another exemplary embodiment.

FIG. 2 is a block diagram illustrating a medical system according to another exemplary embodiment.

In FIG. 2, a medical room 50 is depicted which may include a patient and a number of devices 51*a* . . . 51*n* that may be hooked onto the patient. The devices 51*a* . . . 51*n* may include a first device which measures the heart rate, a second device which measures the blood pressure, a third device which measures oxygen levels, a fourth device which measures the respiratory rate, a fifth device which measures temperature, a sixth device which measure blood flow and temperature at a particular body part of the user e.g., where the surgery occurred. This is provided by way of an example only and not by way of a limitation, one of ordinary skill in the art would readily appreciate that other devices may be provided or the above-noted devices may be integrated into one or more devices.

The medical room 50 may include one or more audio/video (A/V) recorders 61*a* . . . 61*n*. For example, a first A/V record may record only particular events. For example, a recording by the first A/V recorder may be triggered with a touch of a particular body part of the user. A recording by the second A/V recorder may be triggered by a particular event, a recording by a third A/V recorder may be continuous e.g., while a patient is present in the room. This is provided by way of an example and not by way of a limitation. One of ordinary skill in the art would readily appreciate that one or more of these recorders may be integrated into a single recorder. Further, one of ordinary skill in the art would readily appreciate that additional recorders may be provided for various angles, devices, and so on.

In FIG. 2, a communication interface 71 is provided which may encode data and/or multiplex it together to transmit to an analysis server or servers 91. In an exemplary embodiment, the communication interface 71 will send data with a time stamp that may be added by a controller 81 or each respective device.

The server 91 may include one or more servers that may be distributed via cloud computing. The server 91 standardizes data into predetermined format and archives the data into various datastores 101, which may also be distributed. In an exemplary embodiment, in addition to storing these data into various datastores 101, each normalized data is formatted so as to become searchable metadata. The searchable metadata may be stored in a separate archive 101*n*.

Figures 3, 4:
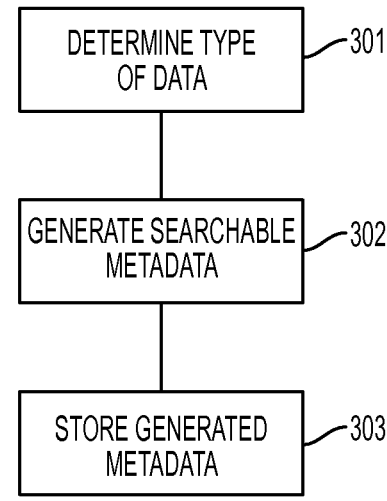
FIG. 3 is a flow chart illustrating a method of generating metadata based on raw data according to an exemplary embodiment.
FIG. 4 is a view illustrating a table showing metadata to generate for a given data type according to an exemplary embodiment.

FIG. 3 is a flow chart illustrating a method of generating metadata based on raw data according to an exemplary embodiment. In FIG. 3, in operation 301, an analysis application or a metadata generation application may analyze the received raw data to determine type of data. For example, type of data may be determined based on a source of data e.g., the device from which it is received, and/or its data type.

For example, if video stream is received, the application determines that the data type is an A/V recording. Next, based on information in the header of a packet in which the data is received, it may determine date and time and which of the A/V recorders recorded the data. By way of another example, it may analyze the actual content to determine type of the recording. For example, angle of recording with respect to the patient may be used to determine type of video stream and the recording device.

Once a data type is determined, searchable metadata is generated based on the determined data type, in operation 302. In other words, additional field or fields are generated with labeled parameters to indicate a part of data that is searchable. For example, if the video stream is determined to be part of post-operative procedure, additional fields may be generated such as [first post-operative check, location of where the video stream is stored—URI], which may then indicate that once the search criteria "post-operative check" is input, this video stream will be provided in the search results based on the added field. Another field that may be generated is [foot surgery, URI of the video stream]. Accordingly, once the search criteria "foot surgery" is input, this video stream will be obtained. Another criteria may be linked to time and date and patient identification [11 am-12 pm, 11/11/11, Smith J, 123456, URI of the video stream]. The generated metadata for the searching is then stored in one or more datastores, in operation 303.

According to another exemplary embodiment, if the data type is determined to be metric data from a heart rate monitor, for example, the metadata may be generated as follows. Generate [heart rate, URI—location of where the metric data is stored]. Another field may be generated for the time and date and patient identification, as explained above. Also, although URI to the data is provided in an exemplary embodiment, the actual data may be identified with the generated metadata instead such as [heart rate, 130, 60].

In another exemplary embodiment, the types of data is preset e.g., based on extension type of the file received. With capturing from a patient monitor, the field/value pairs are named and date/time stamp may be added or a time stamp from the transmission packet may be used. If data is received from an integrated data source, the system maps certain known fields from the source into its standardized format/data type. In an exemplary embodiment, the system may also create or generate custom fields.

FIG. 4 is a view illustrating a table showing metadata to generate for a given data type according to an exemplary embodiment.

That is, in an exemplary embodiment, searchable metadata may be generated for multiple devices of captured data. In FIG. 4, type of data is shown in field 401 and metadata types to be generated in field 402. For example, data types may include video, audio, metric values, images such as X-rays and MRIs. This is provided by way of an example only and not by way of a limitation. Other data types currently known in the industry or later discovered are within the scope of an inventive concept.

For each data type, various metadata may be generated. For example, for the video data type, generated metadata may include date and time the video was generated, patient ID, title of the video such as foot surgery or physical examination, A/V stream data type, from Device 1 at 45 degree angle. For audio data type, generated metadata may include date and time the audio was generated, patient ID, and title of the audio data such as stethoscope, left lung. For metric values data type, the generated metadata may include date and time, patient ID, source of data such as heart monitor A, and type such as [average, lower, highest heart beat]. For images data type, the generated metadata may include date and time, patient ID, source of data such as MRI equipment 001, body part such as head, illness suspected such as tumor. Accordingly, by determining the data type, the system may refer to the table shown in FIG. 4 and generate appropriate metadata. As explained above, information for the metadata may be extracted from the actual data and/or header for the data or data packets in which the data is transmitted for analysis.

In an exemplary embodiment, once the metadata is generated, it is stored in a datastore for further searches and analysis. The searches may be performed as described in greater detail below according to an exemplary embodiment.

Device 1 is a patient monitor that tracks patient's heart rate, blood pressure, oxygen levels, respiratory rate, and temperature. Device 2 is a perfusion monitor that detects changes in blood flow and temperature of the local site. The use of a perfusion monitor can help in the detection of vasospasm in neurosurgical operations. For example, patients with aneurysmal subarachnoid hemorrhage (SAH), or bleeding around the brain, may develop a serious complication known as delayed cerebral ischemia (DCI), or death of brain tissue, which may lead to post-operative stroke and/or death. The onset of DCI is sometimes characterized by the presence of vasospasm and thus, detecting this condition early may reduce the chances of post-operative complications.

According to an exemplary embodiment, a search may be conducted to find all sessions where the below noted condition occurs at least 2 times within a session:
Patient's systolic blood pressure is between 140 and 210 and diastolic blood pressure is between 90 and 125 pressure (Device 1) AND/OR cerebral blood flow (perfusion rate) is less than 50 ml/100 g/min (Device 2)

While specific values can certainly indicate a condition, a rapid change can also indicate issues. Thus, other search criteria may include: find instances where the cerebral blood flow decreases more than 7 ml/100 g per minute. A user may input multiple search criterion and tying them together using "and," "or," and "and/or". In addition, the search criteria may include conditional phrases such as "if blood pressure is above 140, find all instances of cerebral blood flow being less than 50 ml/100 g/min, else all instances of cerebral blood flow being less than 40 ml/100 g/min." In an exemplary embodiment, the user may also input the above-noted exemplary condition as [blood pressure and cerebral blood flow] OR [cerebral blood flow].

Figure 5A:
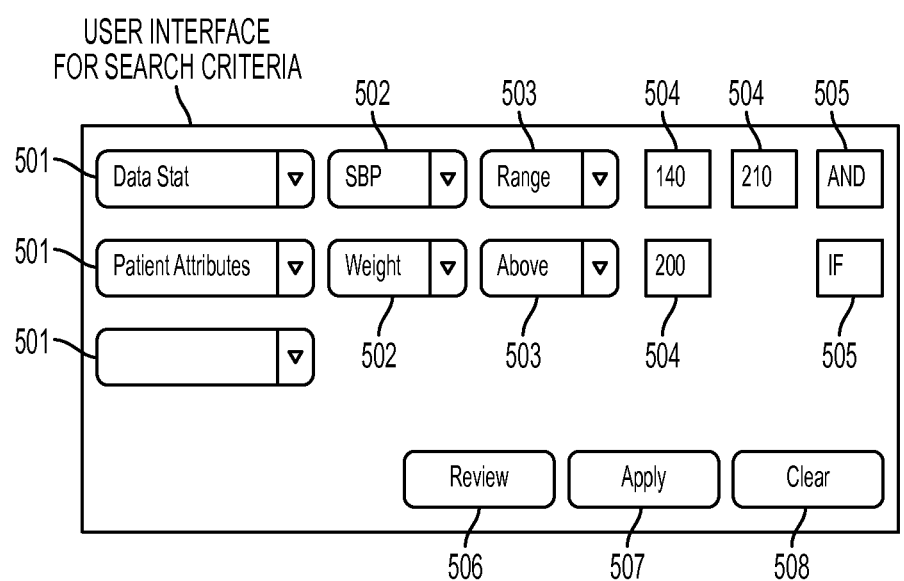
FIGS. 5A and B are views illustrating user interfaces for performing a search according to an exemplary embodiment.

FIGS. 5A and B are views illustrating user interfaces for performing a search according to an exemplary embodiment.

In FIG. 5A, the search criteria may be specified using a drop down menu items and inputting specific values. In the field 501, the user may select, by way of an example, data statics, patient attributes, and so on. Next, in the field 502, the user may select a particular data statics such as stoic blood pressure (SBP) if data statistics was designated in the field 501. In an exemplary embodiment, data statistics include heart rate, oxygen level, cerebral blood flow, or a utterance of a particular audio command. Patient attributes may include patient's age, weight, height, a particular condition e.g., diabetic, and so on.

In the field 503, the user selects what type of values to input for the selected data statistic or patient attribute. For example, the user may select: range, above, below, exact value, and so on. In the field 504, the user may input the desired values such as values for the range, or a particular value. In the field 505, the user may select additional criteria for the search. For example, in the field 505, the user may input an "and" and the next field 501 is generated for user selection. The user may input an "or" or "and/or." Further using the field 505, the user may designate a more complex search criteria. For example, the user may select "if", "else", "only if", "then", "exclude" and so on. This is provided by way of an example only and not by way of a limitation.

In an exemplary embodiment, depending on the data selected in a first field, the subsequent field(s) and data available for selection therein may be different. In an exemplary embodiment, the additional search criteria are dynamically generated on the fly based on a preceding user selection. In an exemplary embodiment, a user selection of a particular field for the search criteria may determine subsequent fields provided to the user for selection. Accordingly, complex search criteria may be designated by a user. To avoid possible mistakes, once the criteria is input, the user may select "review" field 506. A pop box may then be generated which will provide the search criteria in user friendly sentence such as "find stoic blood pressure in a range of 140 to 210 and if weight is above 200 . . . ". The user may clear 508 the search criteria and start over or apply 507 the search criteria. If the user selects to apply 507 the search criteria, a search is conducted based on the user input. On the other hand, if the search criteria are incomplete or incorrect, an error message may be generated.

As similarly shown in FIG. 5B, a search can be conducted to find sessions based on any combination of data or data events from one or more medical devices. In FIG. 5B, the user interface includes a search criteria input section 509 such as the one described above with reference to FIG. 5A and a search results section 510. In FIG. 5B, the first two items, "SBP" and "DBP" shown in section 509, are captured from one device, namely a patient monitor. The third item, "CBF", is captured from a second device, namely a perfusion monitor. The last item, "Age", is captured from a third device, namely the screen of an electronic medical record.

The user may further select additional "data types" and other metadata fields for a search, as explained above. This may be provided via a drop down menu item such as the one shown in FIGS. 5A and 5B. In yet another exemplary embodiment, the user may specify data types by typing in the name using a keyboard and other input devices currently known or further developed. For any data captured by the system, the user can specify search values.

In an exemplary embodiment shown in FIG. 5B, the use of the "between" and "less than" operators is illustrated, but other operators, such as "greater than", "equal to", "not equal to", and so on may also be used. Additionally, rates of change, i.e. specific change in value over a specific length of time, or overall change, can also be used as a specified numeric value for search criteria.

In the above described exemplary embodiment, data from all devices are searched. If a session contains data that meet the search criteria, then that session is included in the search result, and is displayed in section 510. The user can then view that session. The session may contain the captured A/V sources and data captured from any other devices. If the data from other devices are events, i.e. something that occurred at specific time(s), the metric data will be played back with the A/V sources so that all timed data are displayed together. If the data is from the other devices not events, i.e. age, weight, then that data will be displayed as part of the session data.

In another exemplary embodiment, the user may want to highlight certain parts of a session, namely locations where data matches the search criteria. Although the search results provide an entire session, for user's convenience, automatic annotations can be added to the points in time that match the search criteria. These annotations are displayed on the session timeline and can be clicked on to jump to that particular point in the session.

Specifically, in an exemplary embodiment, when data is found that meets the search criteria using the generated metadata stored for the data, the data is further examined to find specific locations that meet the search criteria. Once a location that meets the search criteria is identified, new data called annotation is generated. The annotation data type includes [location, name for the annotation, action to be performed]. For example, action to be performed may be to highlight this portion in a data stream during display and/or playback.

In an exemplary embodiment, the search results list 510 may include an additional column which would identify occurrences or number of events that meet the search criteria. For example, this additional column may indicate number of occurrences that met the search criteria, which will be an integer n>0. Further, an additional column may be provided to provide where in the session the event occurred e.g., at 72 seconds, at 82 seconds, and 2 min, 5 sec. and so on.

That is, the search results may be provided by simply extracting an entire file, which matches the search criteria. For example, an entire recording of a session and all metric data from a blood pressure measuring device may be provided as long as the files contain data therein that meet the user specified search criteria. The occurrence of the search criteria in the found files may be emphasized, as explained above. Automatic annotations are added to a video stream to show occurrence of the search criteria in the session. Metric data may be highlighted, displayed in different color, size, font, or so on to emphasize the found search criteria in the session.

In another exemplary embodiment, the user may want to extract only certain parts of a session that match the search criteria. Based on default or preset times, certain lengths of session clips containing matches to the search will be compiled into a single, easy to navigate list. The user can then only view highlighted parts of the session rather than full sessions. This list may be obtained after the search results are displayed or may be specified along with the search criteria. In an exemplary embodiment, the user may specify the length/duration of the data to include in the clip. For example, the user may specify to show the heart rate for 2 minutes prior to the found search criteria (e.g. 180 heart rate) and 2 minutes after this found search criteria. Accordingly, the clip of data would include the search criteria and the heart rate 2 minutes before and after the found search criteria.

In an exemplary embodiment, new files are generated to provide the search results or the extracted data of interest. The user may set filters such as the one described above. Filters may be more complex such as if the heart rate is 190 somewhere in the 2 minutes before or after the found search criteria, extend the clip to 4 minutes from the found instance of 190. That is, in an exemplary embodiment, the filters for generating new files that provide clips of data may be layered. In an exemplary embodiment, additional sub-filters for the clip may be provided. These sub-filters will vary the length of the clip. In other words, the size of new files may depend on additional, complex filters (sub-filters). Accordingly, in an exemplary embodiment, when an occurrence that matches the search criteria is located, the necessary portion of the A/V stream is extracted and a new file is generated. Similarly, based on the search criteria, a preset number of measurements may be extracted and a new file generated.

In yet another exemplary embodiment, instead of generating a new file, a data field may be generated which would include pointers to locations in an existing session. For example, search results may include: session A, pointer to 3 min, 2 sec [start time], pointer to 6 min, 23 sec [end time]. In an exemplary embodiment, search results are generated on the fly for the sessions or portions thereof that meet the search criteria.

This is provided by way of an example and not by way of a limitation. The user may further set filters such as dates and times, a patient identifier or by criteria such as patients with surgery X in a time period Y.

In an exemplary embodiment, multiple search criteria obtained from a number of devices may be used to provide accurate search results. The search criteria are matched to the metadata to provide accurate search results.

Figure 6:
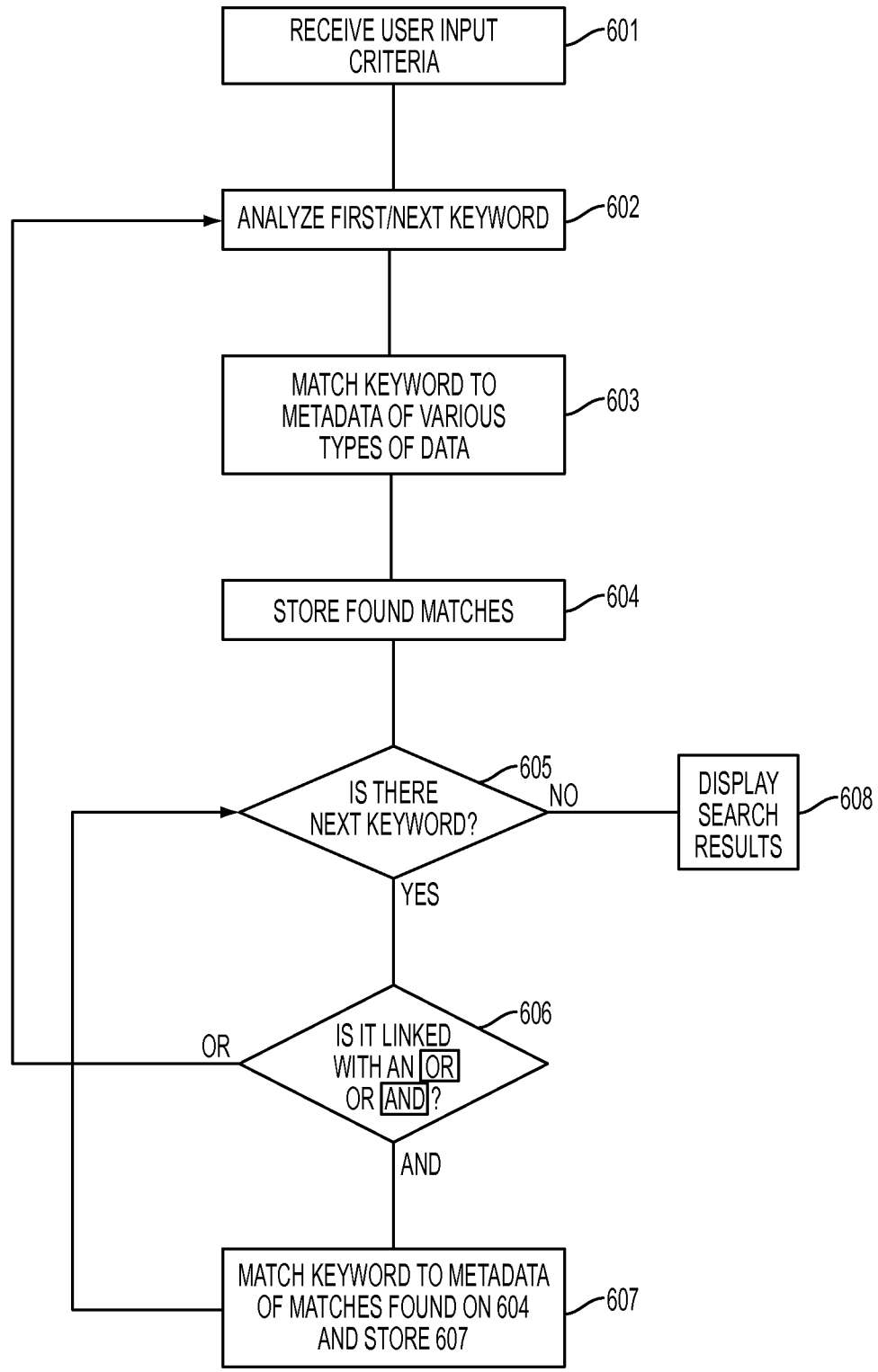
FIG. 6 is a flow chart illustrating a method of searching for data using search criteria applicable to multiple devices according to an exemplary embodiment.

FIG. 6 is a flow chart illustrating a method of searching for data using search criteria applicable to multiple devices according to an exemplary embodiment.

As shown in FIG. 6, in operation 601, the input search criteria are received. In operation 602, first key word in the input search criteria is analyzed. For example, the first input search field may be "blood pressure above 170". Accordingly, the first criterion of "blood pressure above 170" is extracted. In operation 603, the metadata for various types of data are analyzed to find "blood pressure". For each found data that has "blood pressure" as one of the metadata values, the data is examined to find instances where the blood pressure is above 170. If the match is found, the data is stored in a datastore or a temporary memory in operation 604. In an exemplary embodiment, the data that meets the first search criteria is stored in the results list. The system then checks if there is another keyword in the search criteria. If there are no more search criteria fields (Operation 605—No), the system then displays the search results in operation 608.

On the other hand, if additional search criteria are present, the system then determines the relationship between the first search criteria and the additional search criteria i.e., the second criterion. If the two are linked with an "AND", the system searches for matches in the stored search results list. Once a match is found, it is stored in a new search results list. As an alternative exemplary embodiment, each entry in the search results list is analyzed and either deleted or maintained based on whether it matches the second criterion. Accordingly, the search results list is modified to only include data that meets both criteria.

If the first criterion and the second criterion are linked with an "OR", the second keyword is analyzed in operation 602 and the system searches for matches in operation 603. When a match is found, it is added to the search results list in operation 604. In addition, prior to adding the found data to the search results list, the system checks if the data is already present in the search results list. If the data already exists in the search results list, it is not saved again to avoid redundancy.

In an exemplary embodiment, additional operations may be performed to bookmark location of each match. Additional data may be generated and stored in memory for the newly created annotation and/or bookmark.

Video Playback with Trending of Audio/Motion Levels

In an exemplary embodiment, to improve accuracy of the search results, data may be filtered to avoid noise. That is, in an exemplary embodiment, data is adjusted to remove the noise from data. For example, noise may be accounted for in the audio/visual data. Similarly blurriness may be accounted for in image data.

Additionally, audio levels may be filtered for normal activity in the room to detect triggering events. In an exemplary embodiment, the system may determine that an audio level or a particular sound is present in the room e.g., working heater, monitoring equipment, running water, and so on. Accordingly, the audio level will be adjusted to filter this activity in the room. As a result, more accurate detection of triggering events is facilitated.

In an exemplary embodiment, the system continuously monitors the audio/motion level in any given capture environment. In doing so, it can collect data about the audio/motion levels at all times, thereby allowing for baselines or normal levels to be established. These levels are dynamic and can fluctuate with different factors in the environment, such as time of day since more normal noise level may occur during certain times than others.

Accordingly, in an exemplary embodiment, an accurate baseline for a particular element is established by filtering noise. In an exemplary embodiment, a particular data type i.e., element may be tracked in various data streams. For example, trending of various elements such as audio, motion, a particular image in a video stream may be performed, as detailed below.

Trending allows for tracking a particular element across various data types and linking various data types based on the selected element. In an exemplary embodiment described below, trending is performed with respect to audio data. This is provided by way of an example only and not by way of a limitation.

As with data events, an exemplary embodiment allows video playback along with a graph that shows the trending of audio/motion levels. The graph plays along with the video and links the current audio/motion level with a specific point in time of the video, as shown in FIG. 7.

Figure 7:
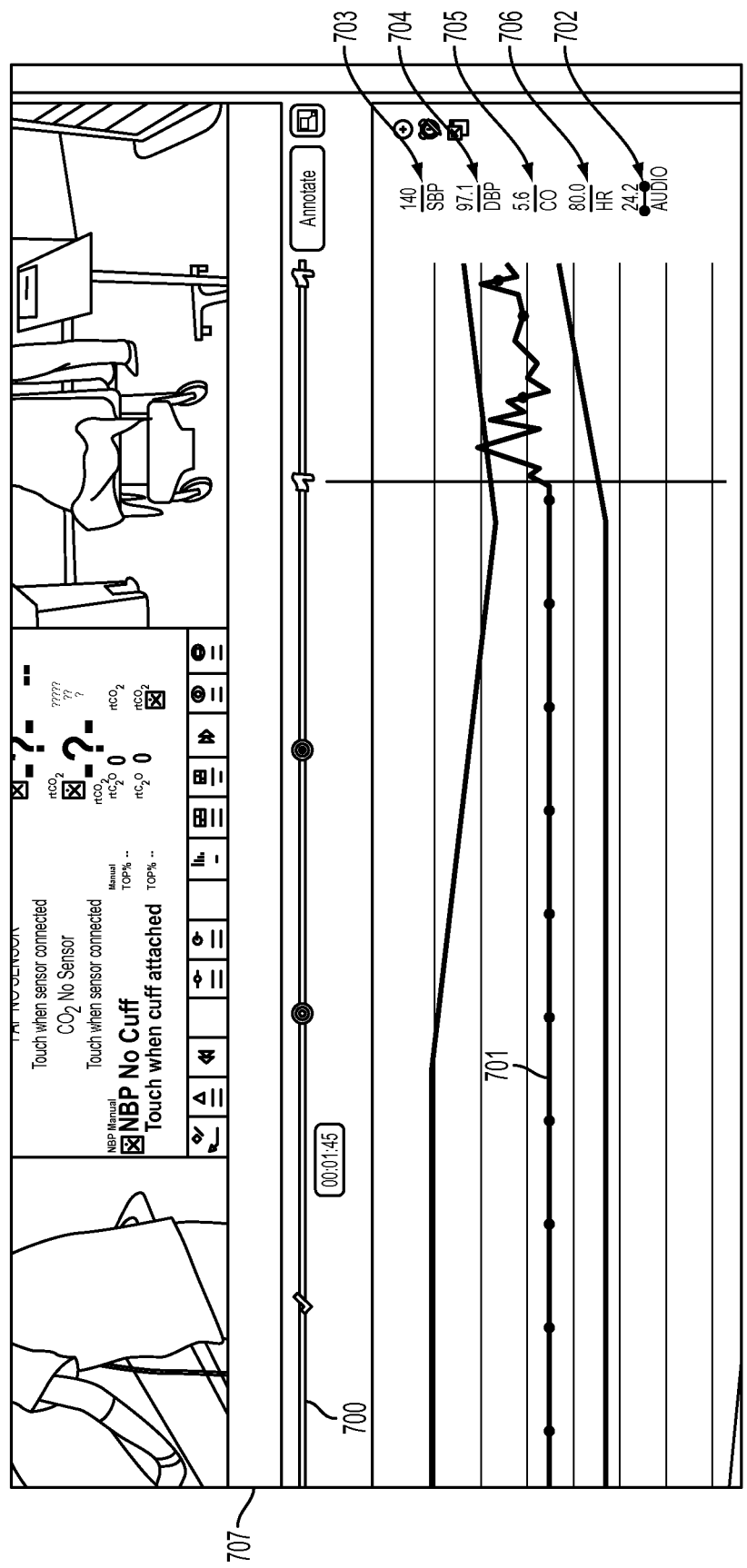
FIG. 7 is a view illustrating a video playback of a captured session with the trending of the audio levels according to an exemplary embodiment.

FIG. 7 is a view illustrating a video playback of a captured session with the trending of the audio levels according to an exemplary embodiment. As shown in FIG. 7, a trend line of the audio levels 700, the dotted line 701 and the field name "AUDIO" 702 are provided as analysis data for the display. The trend line 700 indicates annotations i.e., points where the triggering events e.g., audio activity, occurred. Using the trend line 700, the user views where audio activity occurs in the session and can immediately jump to that point in the video. In an exemplary embodiment, the user may further click on a point of interest on the dotted line 701 (showing the audio level) and the video stream and other displayed statistical data will move to that point. Since the video stream of the session is provided in an integrated form with timeline graphs, the user may simply click on a point of interest e.g., on the audio trend line 700, and the session will jump to this point along with the corresponding timeline graphs 701, . . . , for various elements. Audio levels are provided by way of an example only and not by way of a limitation. In an exemplary embodiment, trending of several elements may be performed. For example, trending may also include SBP element 703, DBP element 704, CO 705, and HR 706. These trending elements are synchronized with the video steam 707. Accordingly, a more detailed analysis of the patient's condition or session may be provided by using various trending elements being linked to the video stream.

Figure 8:
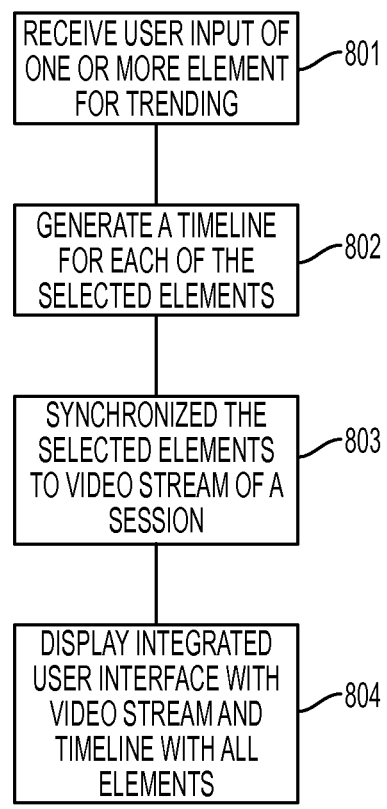
FIG. 8 is a flow chart illustrating a method of trending one or more elements according to an exemplary embodiment.

FIG. 8 is a flow chart illustrating a method of trending one or more elements according to an exemplary embodiment.

As shown in FIG. 8, user input is received for one or more element in operation 801. That is, the user designation of one or more elements that are to be used for trending is received. For example, the user may designate audio, heart rate, blood pressure, and so on, as elements used for trending. In operation 802, based on predefined or user defined filters, timelines are generated for various elements. In an exemplary embodiment, the user may designate various elements and a timeline for each of the selected element will be generated in operation 802. Each element may be designated with its own type of line and a map may be provided, as shown in FIG. 7. In operation 803, the elements are synchronized with a video stream of the session and the generated trendline that may show locations of the events that meet the search criteria. In operation 804, an integrated user interface is displayed. In this integrated user interface, the video stream is played synchronously with a trendline and timelines which depict the selected elements. A value for each of the selected elements is depicted synchronously with the video stream.

Accordingly, in an exemplary embodiment, trending for elements may be generated. The system may automatically assign various types of lines for each of the selected elements or components. The lines may be color coded, different in shape, and size. In addition, in an exemplary embodiment, the user may annotate a particular point on a trendline, which may then be used to generate metadata i.e., additional search criteria for the given component and the video stream. The user may also select one or more timelines (e.g., via dragging, clicking, sliding, selecting via a menu, and so on) and generate metadata that is applicable to these various components. For example, heart rate and blood pressure may be selected and the annotation may be a "heart attack". Based on this annotation, metadata "heart attack" is generated, which is linked with a URI of heart rate at point X and with a URI of blood pressure at point X, and with a URI of video stream at point X and so on. This is provided by way of an example only and not by way of a limitation.

Further, in an exemplary embodiment, the integrated interface allows the user to skip to certain points in the video by clicking on the trendline.

In an exemplary embodiment, with the data levels captured to establish baselines, the system can then automatically and dynamically set thresholds to indicate if the audio/motion level correlates with activity occurring in the captured environment. Users may also manually set these baseline levels as well as the thresholds. A threshold may be specific values, a range, or even an overall change in value. For example, if the audio level is above a value X, the patient is in a critical state "code blue". Further, in another exemplary embodiment, voice recognition may be used when audio levels are above the threshold value to identify the emergency situation and generate an appropriate label. In an exemplary embodiment, an automated annotation may be provided and generated into a search criteria. In an exemplary embodiment, the data may further be analyzed to determine false positives. For example, "code blue" may have been generated because one or more of the monitoring devices malfunctioned. Based on further audio command "false alarm", which is recognized by the system, the data may be deleted.

Event Tracking and Portfolio

In an exemplary embodiment, the user may search for multiple sessions based on common data events groups but otherwise unrelated sessions. Collective review of these sessions can reveal other common factors that led up to the data events and highlight points of interest.

For example, the user may search for all sessions in which heart attack occurred. This search would include sessions of different patients and different circumstances that meet the search criteria. The user may then analyze the sessions to detect a pattern or a common factor that led to the heart attack. In an exemplary embodiment, the system may analyze the sessions present in the search results and highlight common factors. In an exemplary embodiment, the system may detect certain patterns and report back to a user in a form of a chart or search results. For example, the system may detect that before an occurrence of the triggering event, each patient or 90% of the patients had high blood pressure. The system may then emphasize this common pattern to the user for analysis.

An exemplary embodiment allows the assembly of searched sessions into a single, viewable portfolio. A portfolio consists of clips of video consisting of the common data events, including user-defined lengths of time prior to and after the event, as explained above. The portfolio is assembled on-the-fly and may include sessions from one or more searches, thereby reducing the time to generate the portfolio and eliminate the need for extraction, downloading, and post-processing. As mentioned previously, automatic annotations can be displayed to show the occurrence of data events in each session.

In an exemplary embodiment, the portfolio is generated on-the-fly based on search results for data events. The portfolio may include sessions from one or more searches. The generated portfolio may be named and saved. In an exemplary embodiment, the portfolio may include pointers to various sessions or events within the sessions, as opposed to storing actual data. A streaming service can play desired clips of video without the need for extraction from the session, downloading, or post-processing. Automatic annotations can be displayed along with the video stream.

Figure 9:
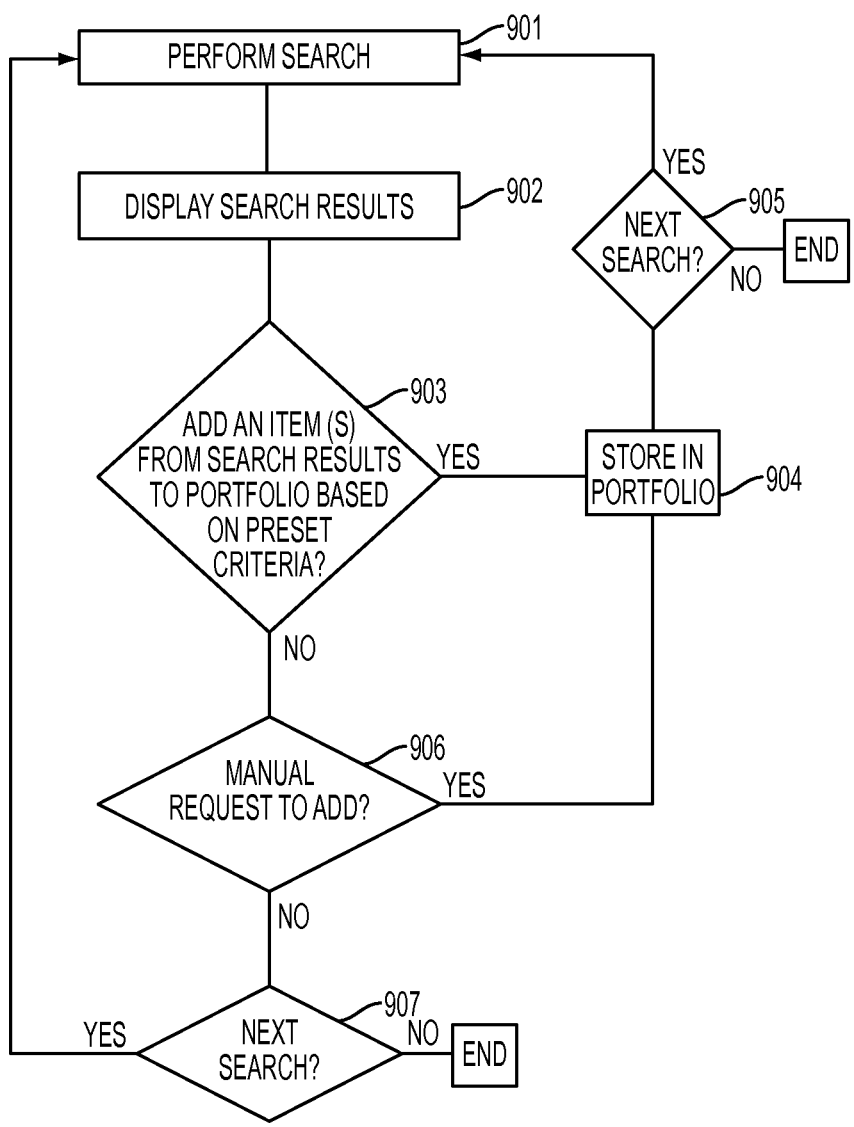
FIG. 9 is a flow chart illustrating a method of generating a portfolio according to an exemplary embodiment.

FIG. 9 is a flow chart illustrating a method of generating a portfolio according to an exemplary embodiment.

In operation 901, a user query with predefined criteria for a search is received. In operation 902, the search results are displayed. One or more items from the search results may be added to a portfolio based on preset criteria. That is, the user may designate various criteria for the portfolio in advance. For example, the user may request that sessions or session clips that contain heart rate above 200 are stored in a portfolio. Based on the predefined criteria—specific requirements/conditions that are set by the user, one or more items from the search results may be added to the portfolio. Specifically, in operation 903, the system checks if each of the items in the search results matches the preset criteria. If the item matches the preset criteria, it is stored in the portfolio in operation 904. Accordingly, the portfolio will include all items from the search results that meet the user-defined criteria.

After the items from the search results are stored in the portfolio in operation 904, the system determines if another search is to be performed in operation 905. If no other searches are to be performed (no in operation 905), then the process ends. On the other hand, if another search is to be performed (yes in operation 905), the system returns to operation 901 in which the search is performed.

In an exemplary embodiment, the user may also manually add one or more items to the portfolio, in operation 906. For example, the user may review the search results and determine that the heart rate of 199 for a duration of ten minutes in session A of the search results is close enough to the preset criteria and may manually add the session A to the portfolio. Next in operation 907, the system determines if another search is to be performed. If so (yes in operation 907), the system returns to operation 901 in which the search is performed. If another search is not requested (no in operation 907), the process ends.

Synchronized, Multi-Channel Event Recordings

In related art, recording in the system is triggered by a user starting a session. In simulation centers where most of the sessions are for training purposes, this is the desired workflow, as there are several components of the session that need to be setup. Users generally also have ample time to prepare and setup the session. However, in a live setting environment such as a doctor's office or a hospital, users are often dealing with patients in time-sensitive situations and may not always have the time to start a recording.

In an exemplary embodiment, the start of multiple channels is triggered for synchronous recordings based on user-defined criteria. These criteria can be a combination of any data captured by the system in real-time, including, but not limited to data from one or more devices. Devices may include medical devices such as a patient monitor, ultrasound machine, and radiology monitors or environmental data such as audio/visual level or activity. For each type of data, criteria may indicate one or more ranges, minimums, maximums, number of occurrences and any combination thereof over any span of time. Any number of these criteria can be combined to define a trigger point for recording. Multiple trigger points can be defined for any given room/area.

In an exemplary embodiment, one mechanism for creating these trigger points can be done similarly to defining the search criteria (shown in FIGS. 5A and 5B). Another exemplary method is shown in FIG. 10, where triggers can be set while defining the data that should be captured via OCR on a specific screen. In an exemplary embodiment, the user may select an appropriate number, and optical character recognition is performed on the selected number and on abbreviations next to the number. Based on the abbreviations next to the number, the source of data may be determined so as to set the trigger, as explained in greater detail below.

Figure 10A:
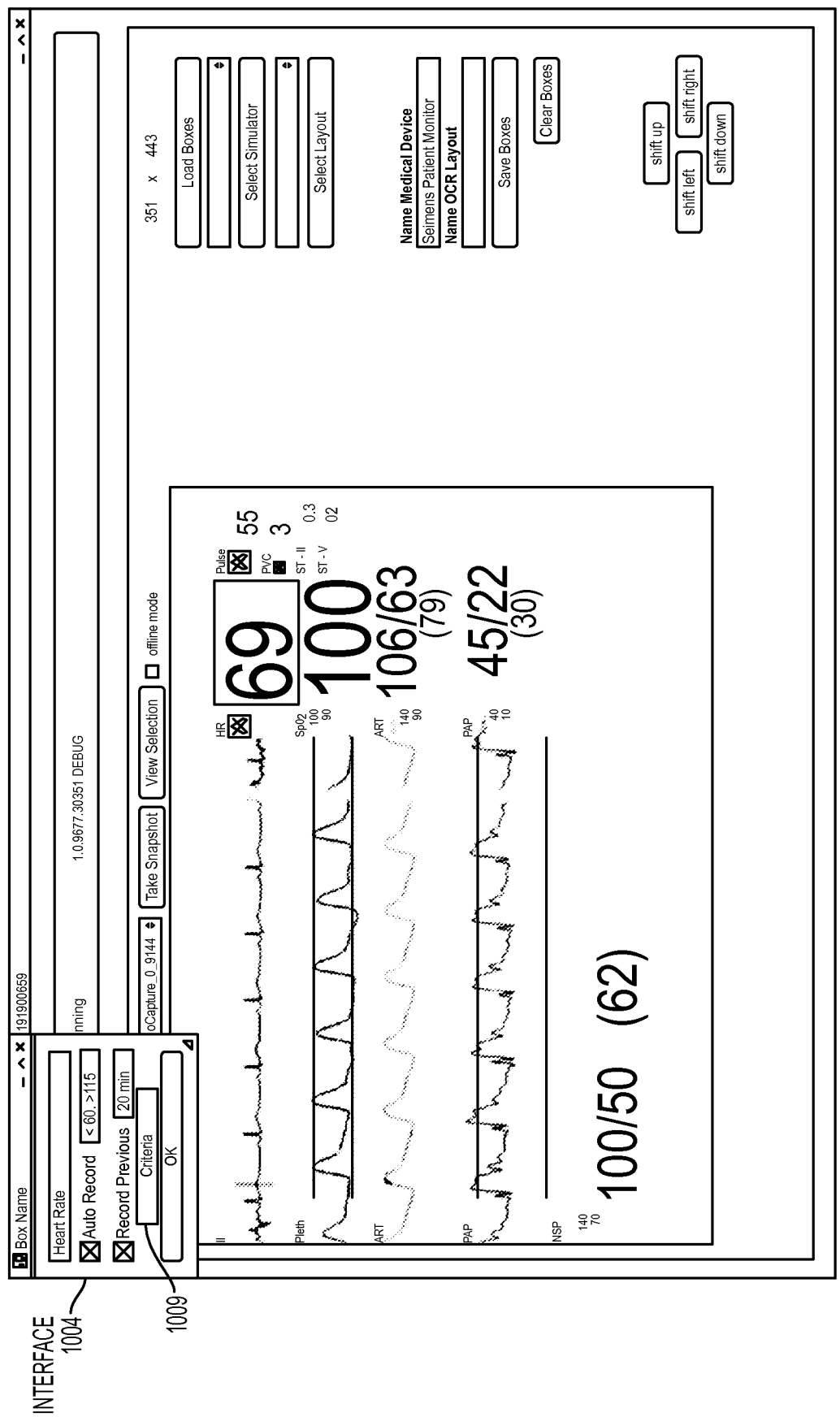
FIGS. 10A-10C are views illustrating user interfaces for setting triggers and defining which parts of a screen to capture via optical character recognition according to various exemplary embodiments.
Figure 10B:
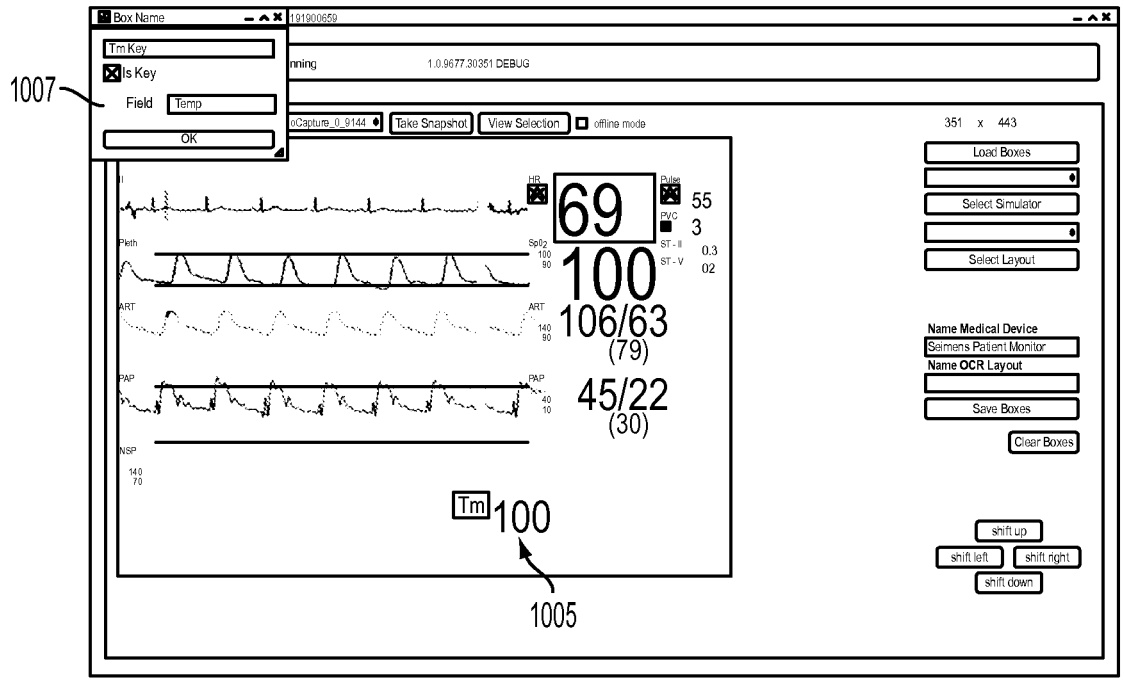
Figure 10C:
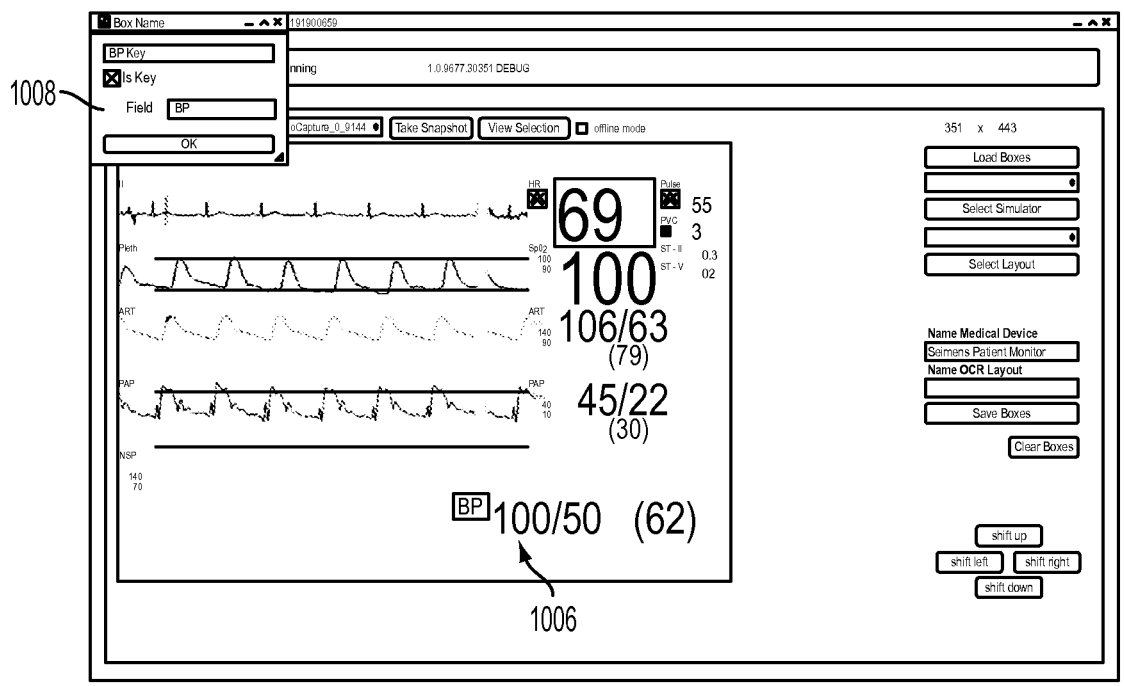

FIGS. 10A-10C are views illustrating user interfaces for setting triggers and defining which parts of a screen to capture via optical character recognition according to various exemplary embodiments.

FIG. 10A illustrates a user interface for setting a trigger while defining which part of a screen to capture via optical character recognition according to an exemplary embodiment. The box 1004 encloses the values to be captured and converted to text. In this case, this value represents the heart rate of the patient. Accordingly, in an exemplary embodiment, the trigger is titled "heart rate" in the box 1004.

The triggers can be set to automatically record when a predetermine value (threshold condition is met). For example, the trigger "Heart Rate" is set to auto record when the value is less than 60 or when it is greater than 115, as shown in the box 1004. Furthermore, the time to record in the "past" can also be set in the box 1004. In an exemplary embodiment shown in FIG. 10A, the previous recording is set to 20 minutes.

In an exemplary embodiment, additional criteria may be set 1009. Additional criteria may be set using additional boxes that could designate additional triggers for the recording and also modify the duration of the previous recordings and so on.

The layout of the parts of the screen to capture as well as the recording criteria can then be saved by giving it a specific name, i.e. Patient Monitor 1A. Thus, multiple layouts for a single device can be defined.

For example, as shown in FIG. 10B, when blood pressure cuff is not attached to the patient, the bottom right part of the screen shows the patient's temperature 1005. However, when a blood pressure cuff is attached, the bottom right part of the screen displays the patient's blood pressure instead 1006, as shown in FIG. 10C. Thus, different layouts are generated so the system knows that one value is temperature and another is blood pressure.

To indicate to the system which layout to use, a "key" is defined that is unique for that particular layout. The system automatically determines which layout to use based on defining a key value. As shown in FIG. 10B, the key "Temp" 1007 is defined when the temperature is displayed. That is, the abbreviation "Tm" 1005 is used by the OCR to determine that the user interface displays temperature. Accordingly, when the system captures data "Tm" using OCR for example, the system will determine that the value next to the "Tm" is patient's temperature.

Similarly, as shown in FIG. 10C, when the blood pressure is displayed 1006, the text "BP" is displayed next to the value. When the system captures the data and sees "BP" as the key value 1008, it knows that value it is receiving is blood pressure i.e. the system will read two values 100/50, as shown in FIG. 10C.

As shown in FIG. 10A, the trigger may combine multiple criteria i.e., outputs of a number of devices. To properly set such triggers, the trigger generation interface may include an add criteria button 1009, which will return the user to the main interface to select another output.

Figure 11:
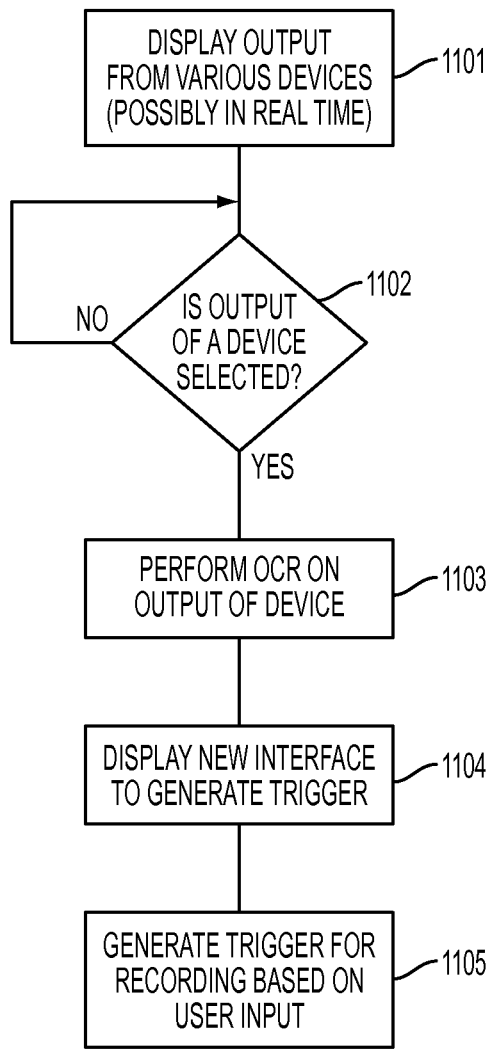
FIG. 11 is a flowchart illustrating a method of setting triggers according to an exemplary embodiment.

FIG. 11 is a flowchart illustrating a method of setting triggers according to an exemplary embodiment.

In FIG. 11, in operation 1101, output from various devices is displayed. In an exemplary embodiment, output from various devices such as blood pressure, heart rate, oxygen level may be displayed in real time. In operation 1102, a user interface is provided in which the user may select a device for generating a trigger. If the device is selected (yes in operation 1102), optical character recognition (OCR) is performed on the output of the device, in operation 1103. For example, if the device is measuring blood pressure, the system will recognize BP as blood pressure and display a new interface to generate a trigger specific to the blood pressure. That is, the new interface may include fields to input minimum and maximum values for the systolic pressure and minimum and maximum values for the diastolic pressure. The generated interface may further include duration, previous recording, and so on. In an exemplary embodiment, based on determining the type of output from the device, a new interface for the trigger is generated.

In operation 1105, the trigger is generated based on user input. Further, in an exemplary embodiment, the trigger with default settings may automatically be generated without additional user input in operation 1105.

Further, in an exemplary embodiment, the trigger may be set for another machine and/or to change a frequency of an event. For example, the trigger may be to increase frequency of a measurements performed by one or more devices e.g., change to measuring blood pressure every minute as opposed to every five minutes when heart rate is above 200.

By way of an example, the following triggers are provided below.

Trigger 1

Start Recording: Heart rate is less than 60 bpm or greater than 115 bpm

Stop Recording: After 15 minutes

In this exemplary embodiment, the user may first select heart rate output displayed on a display. Based on the selected output of the heart rate, the system determines that the device is a heart rate measuring device. Accordingly, a user interface for generating a trigger for the heart rate device is provided. In the generated user interface, the user may input minimum and/or maximum values such as record when heart rate is less than 60 bpm or when it is greater than 115 bpm. The user may further specify a stop recording criteria such as stop recording after 15 minutes. Based on these inputs, a new trigger is generated.

Trigger 2

Start Recording: Patient's systolic blood pressure is between 140 and 210 and diastolic blood pressure is between 90 and 125 pressure AND/OR cerebral blood flow (perfusion rate) is less than 50 ml/100 g/min Stop Recording Patient's systolic blood pressure is less than 140 and diastolic blood pressure is less than 90 AND/OR cerebral blood flow (perfusion rate) is greater than 50 ml/100 g/min for more than 10 minutes In this exemplary embodiment, the user may first select blood pressure output displayed on a display. Based on the selected output of blood pressure, the system determines that the device is a blood pressure measuring device. Accordingly, a user interface for generating a trigger for the blood pressure device is provided.

In the generated user interface, the user may input minimum and/or maximum values or a range for both pressures such as record when systolic pressure is in a range of 140-210 and when diastolic blood pressure is between 90 and 125. The user may further specify a stop recording criteria such as stop recording when systolic blood pressure is less than 140 and diastolic blood pressure is less than 90.

The user may then select to add additional criteria. For the additional criteria, the user will again select one of the displayed outputs from the devices such as cerebral blood flow. The system performs OCR and determines the type of the device. Based on the determined type of the device, an additional user interface for inputting additional criteria for the trigger is generated. For example, the user interface may provide an option to select whether these additional criteria is "AND", "OR", both "AND/OR," or "ANYTHING BUT" with respect to the previously input trigger criteria as it relates to start time and stop time. In an exemplary embodiment, the "AND/OR," option may be selected for the start time and a value of less than 50 ml/110 g/min may be input. Accordingly, whenever one of the first and second criteria is met, the recording will commence.

Additionally, in an exemplary embodiment, the user may further input "AND", "OR", both "AND/OR", "ANYTHING BUT" for the stop recording trigger. The stop recording may be when the cerebral blood flow is greater than 50 ml/100 g/min for more than 10 minutes. These stop criteria may be joined with AND/OR with the first stop criteria. Accordingly, when one of the first stop criteria and the second stop criteria are met, the recording is stopped.

Based on these inputs, a new trigger is generated with multiple criteria for starting and stopping the recording. The trigger, in an exemplary embodiment, involves multiple devices.

Trigger 3

Start Recording: Audio level remains at or above 24 decibels for at least 10 seconds Stop Recording: 5 minutes after the last occurrence of the triggering event In this exemplary embodiment, the user may first select audio level output displayed on a display. Based on the selected output of the audio level, the system determines that the device is an audio recording device. Accordingly, a user interface for generating a trigger for the audio recording device is provided. In the generated user interface, the user may input minimum and/or maximum values and duration such as record when audio level is above 24 decibels for 10 seconds. The user may further specify a stop recording criteria such as stop recording 5 minutes after the last occurrence of the triggering event. Based on these inputs, a new trigger is generated.

In an exemplary embodiment, the trigger generation interface may be such as shown in FIG. 12. As shown in FIG. 12, the trigger 1 will allow recording of an event only when the heart rate and the oxygen level meet the thresholds noted in the trigger. In an exemplary embodiment, the user may further select one or more devices to which the trigger is to be applied. In FIG. 12, the trigger for auto recording and past recording is also shown for each selected output. However, according to an exemplary embodiment, the trigger may be applied to other devices. The user may select a device for a trigger and be provided with a new user interface, where various devices may be specified and the corresponding duration e.g., trigger blood pressure measuring device once or every two minutes until the trigger stop condition is met or trigger a first A/V recorder for ten minutes and a second A/V recorder for five minutes and so on.

By way of an example, the user interface may include a selected displayed output (e.g., heart rate device) for a trigger and a value of 60, for example. The user interface may further include a list of devices for a user to select such as oxygen level measuring device and input auto record and past record for these devices also. That is, in an exemplary embodiment, a trigger may activate another device and/or measurements performed by another device.

In an exemplary embodiment, as explained above, the triggers can also be set to indicate when a session should stop recording. This can be done by setting specific values, a specific duration (stop recording after 15 minutes), or a lapse in time after an event occurs (stop recording 10 minutes after the last occurrence of the triggering event). In related art, recording of a session can only be stopped manually or based on a predefined maximum session time and not based on user defined triggers.

When a recording is triggered to start/stop, the automatic annotations may be added throughout the session to indicate the events that triggered the start/stop of recording as well as any significant events in between.

In another exemplary embodiment, the automatic annotations may further be used to generate metadata for search criteria. In other words, in an exemplary embodiment, the triggering events may also be used to generate metadata. That is, the triggering event will also define search criteria.

In an exemplary embodiment, the user defines trigger criteria/threshold by a combination of any data type. By way of an example and not by way of a limitation, data types may include environmental data such as audio/visual or activity level, data points captured in real-time, triggers for both the start and stop of recording. Automatic annotations may be added to indicate significant events.

Recording in the Past

In simulation centers where most of the sessions are for training purposes, there is a general known start and stop time where users control the start and stop of recording. However, in a live setting, once the need to record is realized, key events may have already occurred. Capture of these prior events may be important to understand what lead to the patient's current condition.

In an exemplary embodiment, past recording is made possible. According to an exemplary embodiment, events that occurred prior to start of recording are also captured. The start of recording may be manual or by a triggered event. Capturing of past events is accomplished by the system always recording and storing video data for a user-specified length of time according to an exemplary embodiment. For example, in an emergency room (ER), events occur fairly quickly and patients do not remain in the ER for an extended stay. Thus, users may choose to only keep video for the past 24 hours. Alternatively, if a patient is in for observation, the doctors may want to keep the video for the past 48 hours, in case they need to review events that led up to a triggering event. Thus, once a session is recorded, the system can include in that session past video capture.

Figure 13:
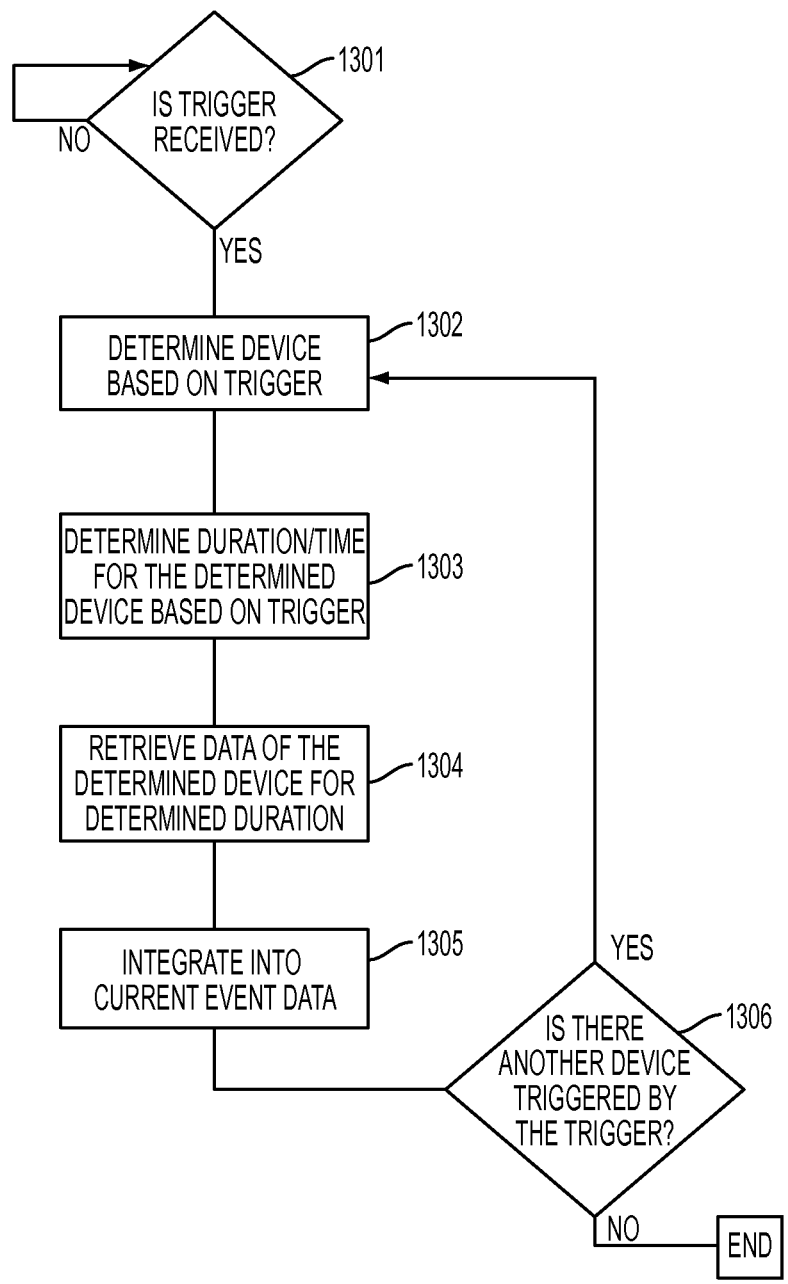
FIG. 13 is a flowchart illustrating a method of combining past recording into a recording of a session according to an exemplary embodiment.

The capture of past video according to an exemplary embodiment is shown in FIG. 13. In an exemplary embodiment, the capture of past data may include A/V recording and/or metric value data.

The length of video or other data in the past is user-defined and can be any length of time. In yet another exemplary embodiment, automatic default duration may be provided.

As shown in FIG. 13, a trigger is received in operation 1301. In operation 1302, a device is determined based on the received trigger. In operation 1303, duration of the recording is determined based on the determined device and the trigger. In operation 1304, data of the determined device for the determined past duration is retrieved. In operation 1305, the retrieved past data is integrated with the current event recording. In operation 1306, it is determined if another device is also triggered by the trigger. If no in operation 1306, then the recording of the session or a clip is complete and the process ends. If yes in operation 1306, the process returns to operation 1302, to determine the next device indicated in the trigger. Accordingly, past recorded data of the specified device or devices is integrated into the current recording.

In an exemplary embodiment, once recording is started, whether manually or triggered automatically by data sets, the actual video would include feed x minutes prior to the start of recording and/or measurements for the past y minutes. If multiple lengths of time are defined for a particular set of video channels, the longest length of time will be used. These lengths of time can vary depending on the triggering events.

Figure 14:
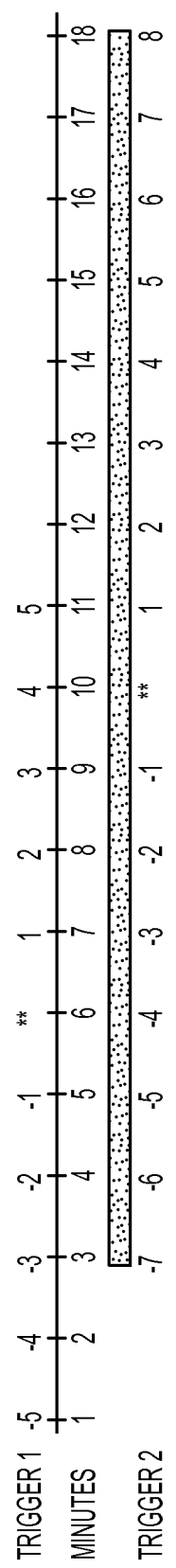
FIG. 14 is a view illustrating duration of recording based on multiple triggers according to an exemplary embodiment.

FIG. 14 is a view illustrating duration of recording based on multiple triggers according to an exemplary embodiment.

As shown in FIG. 14, if the first trigger dictates to record 5 minutes before and 5 minutes after the trigger event, then approximately 10 minutes of recording will be captured. However, if after 4 minutes, a second trigger dictates to record 7 minutes before and 8 minutes after the trigger event, the recording duration will be changed. Because the past recording for trigger 1 gets events prior to the start of past recording for trigger 2, it will record 5 minutes prior to trigger 1. Likewise, since 8 minutes after trigger 2 is longer than 5 minutes after trigger 1, it will record 8 minutes after trigger 2. Thus, the total duration of video will be 18 minutes, as shown in FIG. 14. Lengths of time can be defined for any triggering data sets, specific location, or specific capture device.

Referring back to FIGS. 10A and 12, these exemplary user interfaces provide views for defining previous recording durations to include with the session while defining the OCR capture data. In an exemplary embodiment, the user defines lengths of previous video to include although defaults may be provided. Different lengths can be set for different types/locations of recording and/or other types of data such as metric data.

In an exemplary embodiment, for events triggered by Trigger 1, e.g., heart rate above 200, record for 20 minutes in the past to see why a patient crashed or OCR event such as heart rate spiked past 200 may automatically trigger recording from 20 minutes ago. For events triggered by Trigger 2, e.g., patient's systolic blood pressure is between 140 and 210 and diastolic blood pressure is between 90 and 125 pressure AND/OR cerebral blood flow (perfusion rate) is less than 50 ml/100 g/min, record for 5 minutes in the past. For events occurring outside of the ER, record for 7 minutes in the past. For events occurring in any ER room, record 10 minutes in the past. For events recorded with a capture device #2 (e.g., audio device), record 4 minutes in the past.

Figure 15:
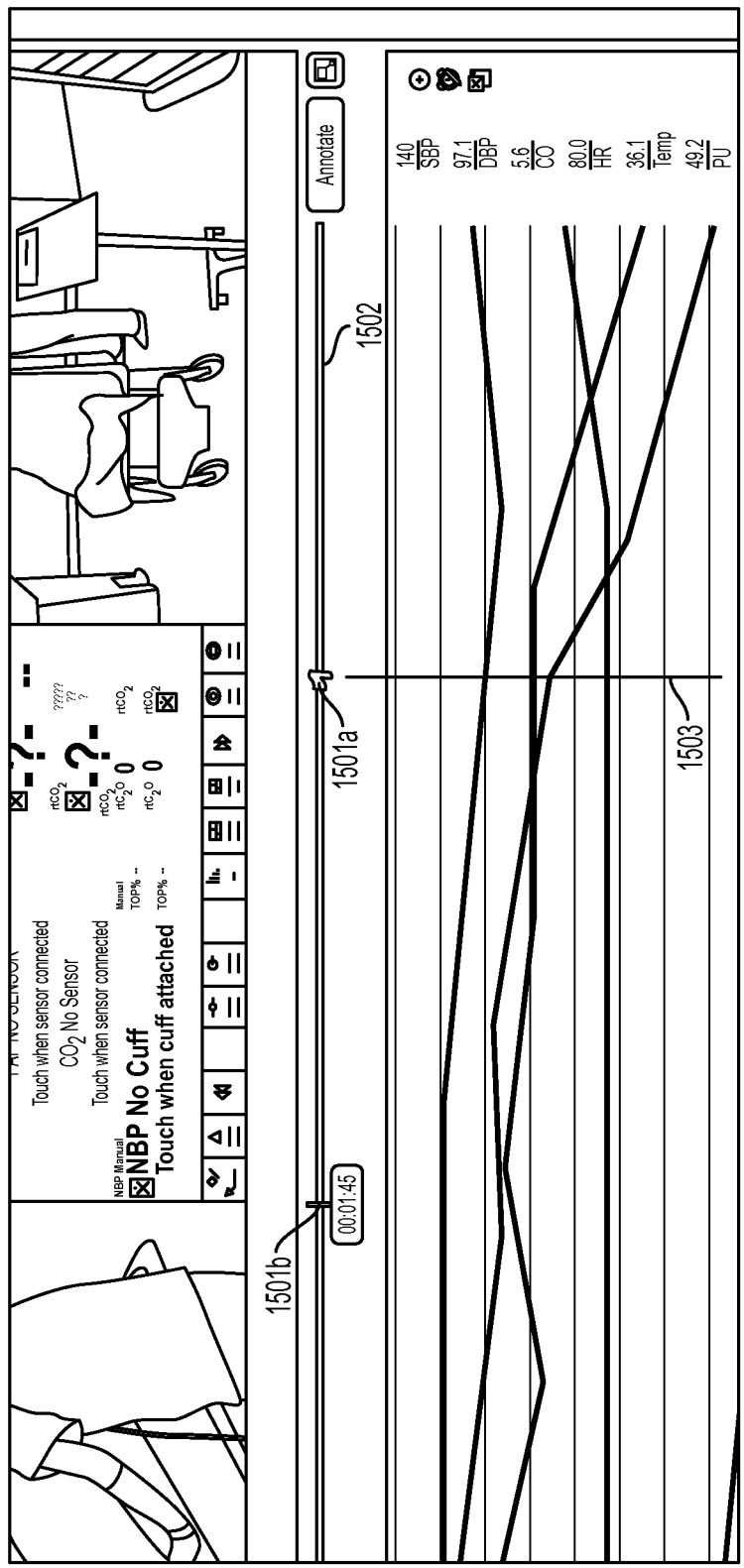
FIG. 15 is a view illustrating generation of an integrated interface based on multi-event trigger according to an exemplary embodiment.

FIG. 15 is a view illustrating generation of an integrated interface based on multi-event trigger according to an exemplary embodiment.

In FIG. 15, a session that was triggered by a combination of data events from multiple devices, i.e. the patient monitor and perfusion monitor, is shown. FIG. 15 illustrates automatic annotations 1501a and 1501b that were added to indicate where the triggering events occurred that began the start of recording as well as the capture of the recordings in the "past". In an exemplary embodiment, the automatic annotation 1501a is emphasized on a trendline 1502 and also on each of the shown timelines using a line 1503. In an exemplary embodiment, line 1503 shows an occurrence of the annotated event on the trendline 1502 and each of the timelines.

In various exemplary embodiments, metadata for raw data from various different medical devices and A/V recorders is generated. This metadata may then be used as search criteria to monitor and track one of more events. In addition, the generated metadata may be used to generate a trendline 1502 i.e. to show trending and annotations 1501a and 1501b. In an exemplary embodiment, the generated metadata may further be used to select elements for a portfolio or to define recording triggers and/or to determine the timing or past time to record an event. This is provided by way of an example and one of ordinary skill in the art would readily understand that the generated metadata may be used to trigger a start of another device and so on. For example, if the generated metadata indicates blood pressure above the preset threshold, it may be used to trigger another device to measure heart rate and oxygen level.

Exemplary embodiments include capturing data from multiple devices and manufacturers. Accordingly, an integrated display of various outputs from various devices may be provided. Further, metadata for the captured data is generated providing for enhanced searches. In exemplary embodiments, a search may be conducted with respect to one or more sessions and/or one or more participants. Based on the generated metadata, the search criteria may be a complex query which combines data from multiple devices.

In addition, in exemplary embodiments, tracking of data may be improved. Specifically, as noted above, user-customized search criteria provide for tracking data using frequency of an occurring event, minimum and maximum values, ranges, and rate of change. Automated annotation may be added to the points of occurrence of the search criteria. In exemplary embodiments, the points of occurrence of event(s) may be flagged based on the search criteria.

In exemplary embodiments, the search results may further be filtered by specifying length of the recording to be provided, whether an entire session is to be provided or a clip based on user-defined filters. Additionally, the session or clip may further be modified to include a past recording.

As a result of this flexibility in searching for data in various sessions and filtering search results by adjusting length of the recording, adding annotations, and so on, trends may be easily detected and quantifiable analyses as well as quality of the analyses may be improved. Further, management of data is facilitated by generating metadata and organizing and structuring data using the generated metadata.

Although above exemplary embodiments are described in a context of medical industry and training, these are provided by way of an example only. The above exemplary embodiments are applicable to actual medical procedures and may be applied to other fields such as security systems and so on. For example, if a break in is detected, the above-described exemplary metadata, triggers, and so on may be helpful in investigating the break in.

An exemplary analysis application such as the one depicted in FIG. 1 may be implemented on a computer-readable medium. The term "computer-readable medium" as used herein refers to any medium that participates in providing instructions to a processor for execution. A computer readable medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable medium would include the following: an electrical connection having two or more wires, a portable computer diskette such as a floppy disk or a flexible disk, magnetic tape or any other magnetic medium, a hard disk, a random access memory (RAM), a read-only memory (ROM), an erasable programmable read-only memory (EPROM or Flash memory), a memory card, any other memory chip or cartridge, an optical fiber, a portable compact disc read-only memory (CD-ROM), any other optical medium, punchcards, papertape, any other physical medium with patterns of holes, or any other medium from which a computer can read or suitable combination of the foregoing.

In the context of this document, a computer readable medium may be any tangible, non-transitory medium that can contain, or store a program for use by or in connection with an instruction execution system, apparatus, or device.

Another form is signal medium and may include a propagated data signal with computer readable program code embodied therein, for example, in a base band or as part of a carrier wave. Such a propagated signal may take any of a variety of forms, including, but not limited to, the electromagnetic, optical, or any suitable combination thereof. The signal medium may include coaxial cables, copper wire and fiber optics, including the wires that comprise data bus. The signal medium may be any medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wire line, optical fiber cable, RF, etc. or any suitable combination of the foregoing.

Computer program code for carrying out operations for aspects of the exemplary embodiments may be written in any combination of one or more programming languages, including an object oriented programming language such as Java, Smalltalk, C+, .Net or the like and conventional procedural programming languages. The program code may execute entirely on the user's computer, partly on the user's computer, as a stand-alone software package, partly on the user's computer and partly on a remote computer or entirely on the remote computer or server. The remote computer may be connected to the user's computer through any type of network, including a local area network (LAN) or a wide area network (WAN), or the connection may be made to an external computer (for example, through the Internet using an Internet Service Provider).

The computer-readable medium is just one example of a machine-readable medium, which may carry instructions for implementing any of the methods and/or techniques described herein. Such a medium may take many forms, including but not limited to, non-volatile media and volatile media. Non-volatile media includes, for example, optical or magnetic disks. Volatile media includes dynamic memory.

Various forms of computer readable media may be involved in carrying one or more sequences of one or more instructions to a processor such as a CPU for execution. For example, the instructions may initially be carried on a magnetic disk from a remote computer. Alternatively, a remote computer can load the instructions into its dynamic memory and send the instructions over a telephone line using a modem. A modem local to a computer system can receive the data on the telephone line and use an infra-red transmitter to convert the data to an infra-red signal. An infra-red detector can receive the data carried in the infra-red signal and appropriate circuitry can place the data on the data bus. The bus carries the data to the volatile storage, from which processor retrieves and executes the instructions. The instructions received by the volatile memory may optionally be stored on persistent storage device either before or after execution by a processor. The instructions may also be downloaded into the computer platform via Internet using a variety of network data communication protocols well known in the art.

The flowchart and block diagrams in the Figures illustrate the architecture, functionality, and operation of possible implementations of systems, methods and computer program products according to various exemplary embodiments. In this regard, each block in the flowchart or block diagrams may represent a module, segment, or portion of code, which comprises one or more executable instructions for implementing the specified logical functions. It should also be noted that, in some alternative implementations, the functions noted in the block may occur out of the order noted in the figures. For example, two blocks shown in succession may, in fact, be executed substantially concurrently, or two blocks may sometimes be executed in the reverse order, depending upon the functionality involved. It will also be noted that each block of the block diagram and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology as used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising" when used in this specification, specify the presence of stated features, integers, steps, operations, elements, and/or components, but do not preclude the presence or addition of one or more other features, integers, steps, operations, elements, components, and/or groups thereof.

The description of the exemplary embodiments has been presented for purposes of illustration and description, but is not intended to be exhaustive or limiting in any form. Many modifications and variations will be apparent to those of ordinary skill in the art without departing from the scope and spirit of the invention. Embodiments were chosen and described in order to explain operations and the practical application, and to enable others of ordinary skill in the art to understand various embodiments with various modifications as are suited to the particular use contemplated. That is, various modifications to these embodiments will be readily apparent to those skilled in the art, and the generic principles and specific examples defined herein may be applied to other embodiments without the use of inventive faculty. For example, some or all of the features of the different embodiments discussed above may be combined into a single embodiment. Conversely, some of the features of a single embodiment discussed above may be deleted from the embodiment. Therefore, the inventive concept is not intended to be limited to the exemplary embodiments described herein but is to be accorded the widest scope as defined by the limitations of the claims and equivalents thereof.

What we claim is:

1. A method of integrating data from a plurality of devices, the method comprising:
   receiving, in real-time, first data from a first device, which records, as video data, values depicted on a monitoring display of a first medical equipment;
   receiving, in real-time, second data from a second device, the second device being a second type of device different from a first type of the first device;
   determining, by a computer, a first type of the first data and a second type of the second data;
   generating additional data based on the first type of the first data and the second type of the second data, wherein the additional data comprises searchable metadata specific for each of the first type of the first data and the second type of the second data and a trigger based on a first value in the first data exceeding a first predetermined threshold and a second value in the second data exceeding a second predetermined threshold, occurring at substantially same time,
   wherein the second device is a second medical equipment that gathers vital signs of a patient or a simulator of the patient in a metric format,
   wherein the trigger is based on at least one value comprising the first value extracted from the video data and the second value indicating the vital signs of the patient,
   wherein at least one of the first device and the second device is controlled to perform an action based on the trigger; and
   converting the first data into a text format by:
      recognizing at least one indicator by performing, in real-time, an optical character recognition on the at least one indicator displayed on the monitoring display of the first medical equipment, wherein the at least one indicator is displayed adjacent to data values and wherein each of the at least one indicator indicates a type of the data values,
      determining the type of the data values based on the at least one indicator corresponding to the data values, and
      recognizing the data values by performing the optical character recognition on the data values corresponding to the at least one indicator,
   wherein the trigger is selected from among a plurality of triggers based on the type of the data values and wherein the data values are compared to the trigger to detect an event, and
   wherein the event indicates a medical condition occurring in the patient or the simulator of the patient.

2. The method of claim 1, wherein the first device and the second device are utilized in a medical procedure or a simulation session of the medical procedure,
   wherein the first device and the second device monitor output from at least two of: the patient, the simulator of the patient, a medical personnel, and a learner, and
   wherein the first predetermined threshold and the second predetermined threshold are input, in advance, by a user via a user interface.

3. The method of claim 1, wherein the generating the additional data comprises:
   extracting information from the first data;
   generating metadata fields for the searchable metadata based on a predefined criteria; and
   storing in a memory the metadata fields along with a location of the first data,
   wherein different metadata fields are generated based on the first type of the first device and the second type of the second device such that the different metadata fields are generated for the first device and the second device, and
   wherein the predefined criteria comprises a structured rule set comprising metadata fields to be generated for each of the first type of the first device and the second type of the second device.

4. The method of claim 3, wherein the first data and the second data are displayed data, and
   wherein the displayed data is converted based on the first type of the first device and the second type of the second device.

5. The method of claim 1, further comprising:
   receiving a user-defined search query;
   searching the first data and the second data based on the additional data and the user-defined search query;
   extracting matching data among the first data and the second data based on whether the additional data matches the user-defined search query;
   generating search results by combining the matching data; and
   outputting the search results,
   wherein the outputting the search results comprises displaying the first data among the matching data on a first portion of a screen and displaying the second data among the matching data on a second portion of the screen such that the matching data from among the first data and the second data are displayed temporally aligned to each other.

6. The method of claim 5, wherein the user-defined search query comprises at least one value for data from a plurality of devices and at least one specified duration of a recording.

7. The method of claim 6, wherein the at least one specified duration of the recording comprises at least one of: a duration of the recording after an occurrence of the event and a duration of a past recording to be integrated with the recording, and
   wherein the event occurs if the data matches the at least one value defined in the user-defined search query.

8. The method of claim 5, further comprising:
   automatically generating annotations in the matching data based on the user-defined search query; and
   outputting the search results with the annotations,
   wherein the annotations indicate points in the matching data meeting user-specified criteria.

9. The method of claim 8, wherein the outputting the search results comprises displaying a user interface for reproducing a recording of a session or a clip of the session provided in the search results synchronously with metric values from at least two different types of sources, wherein the metric values are output in a form of a graph, and
wherein the annotations are provided for each of the recording and the metric values from the at least two different types of the sources.

10. An apparatus configured to integrate data generated by a plurality of different devices, the apparatus comprising:
a processor; and
a memory configured to store instructions, which when executed by the processor cause the processor to control the apparatus to perform:
receiving, in real-time, first data from a first device, which records, as video data, values depicted on a monitoring display of a first medical equipment;
receiving, in real-time, second data from a second device, the second device being a second type of device different from a first type of the first device;
determining a first type of the first data and a second type of the second data;
generating additional data based on the first type of the first data and the second type of the second data, wherein the additional data comprises searchable metadata specific for each of the first type of the first data and the second type of the second data and a trigger based on a first value in the first data exceeding a first predetermined threshold and a second value in the second data exceeding a second predetermined threshold, occurring at substantially same time; and
controlling at least one of the first device and the second device to perform an action based on the trigger,
wherein the first value is extracted from the video data and the second value indicates vital signs of a patient or a simulator of the patient, and
wherein the second device is a second medical equipment that gathers the vital signs of the patient or the simulator of the patient in a metric format, and
wherein the instructions further comprise:
recognizing at least one indicator by performing, in real-time, an optical character recognition on the at least one indicator displayed on the monitoring display of the first medical equipment, wherein the at least one indicator is displayed adjacent to data values displayed on a display and wherein each of the at least one indicator indicates a type of the data values;
determining the type of the data values based on the at least one indicator corresponding to the data values;
continuously converting, in real time, the data values adjacent to the at least one indicator;
selecting a sub-trigger from among a plurality of triggers based on the type of the data values; and
comparing the sub-trigger to each of the data values to determine an occurrence of an event.

11. The apparatus of claim 10, wherein the trigger is for the event indicating a medical condition and comprises a plurality of sub-triggers specific, each for a respective data type,
wherein the instructions when executed by the processor further cause the processor to control the apparatus to perform:
converting the first data to values, continuously, in real-time, and
comparing the values to a respective sub-trigger from among the plurality of sub-triggers.

12. The apparatus of claim 10, wherein the first device and the second device are utilized in a medical procedure or a simulation session of the medical procedure, and
wherein the first device and the second device monitor output from at least two of: the patient, the simulator of the patient, a medical personnel, and a learner.

13. The apparatus of claim 10, wherein the generating the additional data comprises:
extracting information from the first data;
generating metadata fields for the searchable metadata based on a predefined criteria; and
storing the metadata fields along with a location of the first data,
wherein different metadata fields are generated based on the first type of the first device and the second type of the second device such that the different metadata fields are generated for the first device and the second device, and
wherein the predefined criteria comprises a structured rule set comprising metadata fields to be generated for each of the first type of the first device and the second type of the second device.

14. The apparatus of claim 13, wherein the first data and the second data are displayed data, and
wherein the displayed data is converted based on the first type of the first device and the second type of the second device.

15. The apparatus of claim 10, wherein the instructions when executed by the processor further cause the processor to control the apparatus to perform:
receiving a user-defined search query;
searching the first data and the second data based on the additional data and the user-defined search query;
extracting matching data among the first data and the second data based on whether the additional data matches the user-defined search query;
generating search results by combining the matching data; and
outputting the search results.

16. The apparatus of claim 15, wherein the user-defined search query comprises at least one value for data from a plurality of devices and at least one specified duration of a recording.

17. The apparatus of claim 16, wherein the at least one specified duration of the recording comprises at least one of: a duration of the recording after an occurrence of the event and a duration of a past recording to be integrated with the recording, and
wherein the event occurs if the data matches the at least one value defined in the user-defined search query.

18. The apparatus of claim 15, wherein the instructions when executed by the processor further cause the processor to control the apparatus to perform:
automatically generating annotations in the matching data based on the user-defined search query; and
outputting the search results with the annotations,
wherein the annotations indicate points in the matching data meeting user-specified criteria.

19. The apparatus of claim 15, wherein the plurality of sub-triggers comprise a first sub-trigger for at the first type of the first data and a second sub-trigger for the second type of the second data,
wherein, in response to the first value of the first data exceeding the first predetermined threshold, recording values of the first data for a first predetermined duration, wherein, in response to the second value of the second data exceeding the second predetermined threshold, recording values of the second data for a second predetermined duration, wherein the processor executing the instructions is further configured to control the apparatus to integrate the values of the first data and the values of the second data into a single timeline, wherein the first predetermined duration is different from the second predetermined duration, wherein the outputting the search results comprises a user interface illustrating the single timeline, wherein the first predetermined duration comprises a first recording duration, which is a duration before the first value of the first data exceeds the first predetermined threshold, and the second predetermined duration comprises a second recording duration, which is a duration before the second value of the second data exceeds the second predetermined threshold, and wherein the first recording duration is different from the second recording duration.

20. A non-transitory computer readable medium storing instructions when executed by a computer cause the computer to perform:

receiving, in real-time, first data from a first device, which records, as video data, values depicted on a monitoring display of a first medical equipment;

receiving, in real-time, second data from a second device, the second device being a second type of device different from a first type of the first device;

determining, by the computer, a first type of the first data and a second type of the second data;

generating additional data based on the first type of the first data and the second type of the second data, wherein the additional data comprises searchable metadata specific for each of the first type of the first data and the second type of the second data and a trigger based on a first value in the first data exceeding a first predetermined threshold and a second value in the second data exceeding a second predetermined threshold, at substantially same time; and controlling at least one of the first device and the second device to perform an action based on the trigger, wherein the second device is a second medical equipment that gathers vital signs of a patient or a simulator of the patient in a metric format, wherein the trigger is based on at least one value comprising the first value extracted from the video data and the second value indicating the vital signs of the patient; and converting the first data into a text format by:
recognizing at least one indicator by performing, in real-time, an optical character recognition on the at least one indicator displayed on the monitoring display of the first medical equipment, wherein the at least one indicator is displayed adjacent to data values and wherein each of the at least one indicator indicates a type of the data values, determining the type of the data values based on the at least one indicator corresponding to the data values, and recognizing the data values by performing the optical character recognition on the data values corresponding to the at least one indicator, wherein the trigger is selected from among a plurality of triggers based on the type of the data values and wherein the data values are compared to the trigger to detect an event, and wherein the event indicates a medical condition occurring in the patient or the simulator of the patient.

21. A system for processing data from a plurality of devices, the system comprising:

at least one medical monitoring equipment configured to monitor metric output from at least one of: an object and a human, during a session;

at least one audio or video recorder configured to record the at least one of the object and the human, during the session; and a server comprising at least one processor and a memory, the server configured to:
receive first data from the at least one medical monitoring equipment and second data from the at least one audio or video recorder, determine a type of an apparatus based on the first data and the second data, generate additional data based on the type of the apparatus, wherein the additional data comprises metadata specific to the type of the apparatus and a trigger comprising a first sub-trigger which is based on a first value of the first data received from the at least one medical monitoring equipment exceeding a first threshold value and a second sub-trigger based on a second value of the second data from the at least one audio and video recorder exceeding a second predetermined threshold, and setting, by the server, a plurality of different actions for the trigger, wherein the first sub-trigger triggers a first recording of first values of the first data received from the at least one medical monitoring equipment for a first duration and the second sub-trigger triggers a second recording of second values of the second data received from the at least one audio and video recorder for a second duration, wherein the first duration is different from the second duration, wherein the first recording and the second recording are combined to generate a single recording or a single event, wherein the plurality of different actions comprise different durations of recording the first data of the at least one medical monitoring equipment from the second data of the at least one audio or video recorder, wherein the plurality of different actions comprises obtaining a past recording, which is prior to occurrence of the trigger, for at least one of the at least one medical monitoring equipment and the at least one audio or video recorder and combining with a current recording of the first data and the second data, and wherein the trigger is generated, on the fly, based on continuously receiving the first data and the second data, in real-time.

22. The system of claim 21, wherein a duration of a recording for the generating of the single event depends on a device type, and wherein the server is further configured to generate a single timeline indicating the first recording and the second recording.

* * * * *